(12) United States Patent
Arlen et al.

(10) Patent No.: US 11,001,641 B2
(45) Date of Patent: *May 11, 2021

(54) MONOCLONAL ANTIBODY THERAPY FOR PANCREAS CANCER

(71) Applicant: PRECISION BIOLOGICS, INC., Rockville, MD (US)

(72) Inventors: Myron Arlen, Great Neck, NY (US); Kwong Tsang, Bethesda, MD (US)

(73) Assignee: PRECISION BIOLOGICS, INC., Rockville, MD (US)

( * ) Notice: Subject to any disclaimer, the term of this patent is extended or adjusted under 35 U.S.C. 154(b) by 32 days.

This patent is subject to a terminal disclaimer.

(21) Appl. No.: 16/162,731

(22) Filed: Oct. 17, 2018

(65) Prior Publication Data

US 2019/0100601 A1 Apr. 4, 2019

Related U.S. Application Data

(60) Division of application No. 15/417,326, filed on Jan. 27, 2017, now abandoned, which is a division of application No. 14/509,428, filed on Oct. 8, 2014, now Pat. No. 9,592,290, which is a division of application No. 13/011,631, filed on Jan. 21, 2011, now Pat. No. 9,034,588, which is a division of application No. 11/234,645, filed on Sep. 22, 2005, now abandoned, which is a continuation of application No. 10/472,008, filed as application No. PCT/US02/09193 on Mar. 15, 2002, now abandoned.

(60) Provisional application No. 60/276,284, filed on Mar. 15, 2001.

(51) Int. Cl.

| A61K 39/00 | (2006.01) |
| C07K 16/30 | (2006.01) |
| A61K 47/68 | (2017.01) |
| A61K 39/395 | (2006.01) |
| G01N 33/574 | (2006.01) |
| A61K 49/04 | (2006.01) |
| A61K 49/16 | (2006.01) |
| A61K 49/22 | (2006.01) |

(52) U.S. Cl.
CPC ...... *C07K 16/303* (2013.01); *A61K 39/39558* (2013.01); *A61K 47/6859* (2017.08); *A61K 49/04* (2013.01); *A61K 49/16* (2013.01); *A61K 49/221* (2013.01); *G01N 33/57438* (2013.01); *A61K 2039/505* (2013.01); *C07K 2317/14* (2013.01); *C07K 2317/24* (2013.01); *C07K 2317/56* (2013.01); *C07K 2317/732* (2013.01); *C07K 2319/00* (2013.01); *G01N 2333/705* (2013.01)

(58) Field of Classification Search
CPC .............. C07K 16/303; C07K 2317/24; C07K 2317/56; A61K 47/6859; A61K 49/16; A61K 39/39558; A61K 2039/505; G01N 33/57438; A61P 35/00
See application file for complete search history.

(56) References Cited

U.S. PATENT DOCUMENTS

| 4,376,110 A | 3/1983 | David et al. |
| 4,579,827 A | 4/1986 | Sakamoto et al. |
| 4,713,352 A | 12/1987 | Bander et al. |
| 4,737,579 A | 4/1988 | Hellstrom et al. |
| 4,753,894 A | 6/1988 | Frankel et al. |
| 4,816,567 A | 3/1989 | Cabily et al. |
| 4,946,778 A | 8/1990 | Ladner et al. |
| 5,212,085 A | 5/1993 | Wands et al. |
| 5,530,101 A | 6/1996 | Queen et al. |
| 5,585,089 A | 12/1996 | Queen et al. |
| 5,595,898 A | 1/1997 | Robinson et al. |
| 5,665,848 A | 9/1997 | Barnard |
| 5,688,657 A | 11/1997 | Tsang et al. |
| 6,884,679 B2 | 4/2005 | Baca et al. |
| 9,034,588 B2 | 5/2015 | Arlen et al. |
| 9,592,290 B2 * | 3/2017 | Arlen ...................... A61P 35/00 |

FOREIGN PATENT DOCUMENTS

| EP | 0279669 | 8/1988 |
| EP | 0521842 | 1/1993 |
| EP | 0113367 | 2/1993 |
| EP | 0526888 | 2/1993 |
| EP | 1311962 | 1/2011 |
| EP | 1411962 | 1/2011 |
| JP | 7-503124 | 4/1995 |
| WO | 84/00375 | 2/1984 |
| WO | 91/09967 | 7/1991 |
| WO | 92/22324 | 12/1992 |
| WO | 9503828 | 2/1995 |
| WO | 0105427 | 1/2001 |

(Continued)

OTHER PUBLICATIONS

Arlen M, et al. "Identification and characterization of a colon tumor-associated antigen," Ann N Y Acad Sci. Aug. 12, 1993;690:374-5.
Haigh et al., Oncology, vol. 13 p. 1561-1582 (1999).
Freshney, Culture of Animals Cells, a Manual of Basic Technique, Alan R. Liss, Inc., New York, pp. 3-4 (1983).
Derrner, Bio/Technology, 12:320 (1994).
Gura, Science, 278:1041-1042 (1997).
Jain, Sci. Am., 271:58-65 (1994).
Accession No. AAR70828 (Mar. 25, 2003) Database Geneseq, Thompson Reuters, Philadelphia, PA USA.

(Continued)

*Primary Examiner* — Sheela J. Huff
(74) *Attorney, Agent, or Firm* — Robin L. Teskin; Baker, Donelson, Bearman, Caldwell & Berkowitz PC

(57) ABSTRACT

The present invention relates to the use of binding equivalents of monoclonal antibody 31.1, including chimerized and/or humanized versions thereof, antibody fragments as well as competitively binding and co-specific antibodies and antibody fragments, in the treatment of pancreatic cancer.

19 Claims, 12 Drawing Sheets

Figure 1A:
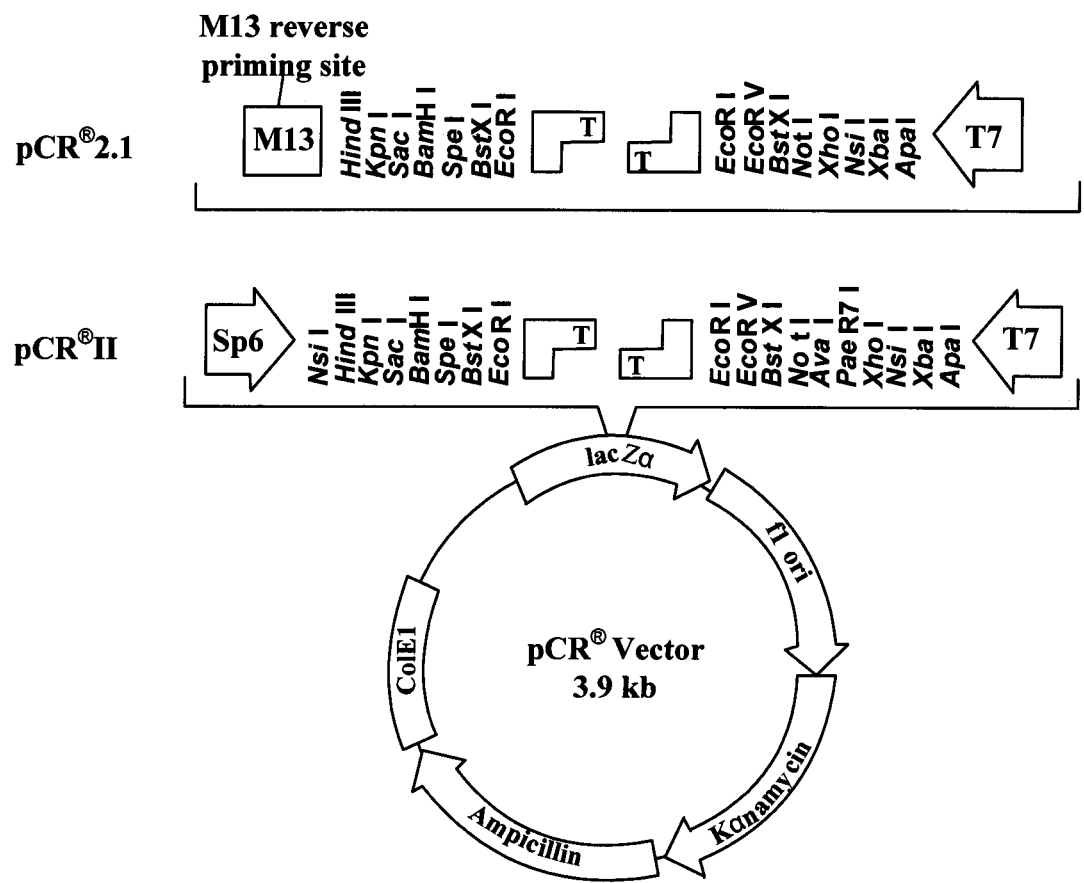
Figure 1B:
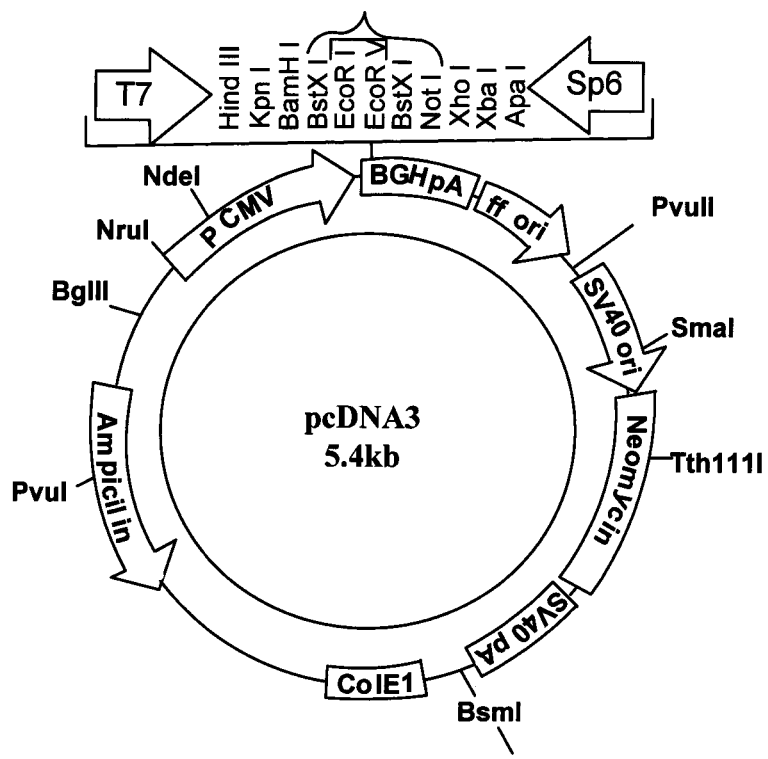

Specification includes a Sequence Listing.

(56) References Cited

FOREIGN PATENT DOCUMENTS

| WO | 02/074251 | 9/2002 |
| WO | 2002074251 | 2/2004 |

OTHER PUBLICATIONS

Accession No. ABR82780 (Dec. 18, 2003) Database Geneseq, Thompson Reuters, Philadelphia, PA USA.
Accession No. AEF82574 (Apr. 20, 2006) Database Geneseq, Thompson Reuters, Philadelphia, PA USA.
Accession No. CAA78741 (Sep. 14, 1992).
Accession No. CAB46325 (Jul. 1, 1999).
Arlen, et al. (1998) Crit Rev. Immunol. 18(1-2): 133-138.
Arlen, et al. (2001) Abstract #P74 entitled "Development of a therapeutic monoclonal antibody against high grade recurrent colon and pancreatic cancer." Presented at the 54th Annual Cancer Symposium, Society of Surgical Oncology, Mar. 15-18, 2001. Washington D.C.
Ausubel et al. (1989) Current Protocols in Molecular Biology, vol. I, Green Publishing Associates, Inc., and John Wiley & Sons, Inc., New York, at p. 2.10.3.
Bird, et al. (1988) Single-Chain Antigen-Binding Proteins. Science 242: 423-426.
Bowie et al. Deciphering the message in protein sequences: tolerance to amino acid substitutions. Science. Mar. 16, 1990;247(4948):1306-10.
Bradbury A. scFvs and beyond. Drug discovery today. Aug. 15, 2003;8(16):737-9.
Burgess et al. Possible dissociation of the heparin-binding and mitogenic activities of heparin-binding (acidic fibroblast) growth factor-1 from its receptor-binding activities by site-directed mutagenesis of a single lysine residue. The Journal of Cell Biology. Nov. 1, 1990;111(5):2129-38.
Chames, et al. (2010) Scientific World Journal 10: 1107-1120.
Christiansen et al Molecular Cancer Therapeutics vol. 3 p. 1493 (2004).
Clark M. Antibody humanization: a case of the 'Emperor's new clothes'?, Immunology today. Aug. 1, 2000;21(8):397-402.
Cole et al. The EBV-hybridoma technique and its application to human lung cancer. Monoclonal Antibodies and Cancer Therapy. 1985;27:77-96.
Cote et al. Generation of human monoclonal antibodies reactive with cellular antigens. Proceedings of the National Academy of Sciences. Apr. 1, 1983;80(7):2026-30.
Creighton, et al. (1993) Proteins: Structures and Molecular Principles (2"d Ed.) [Table of Contents].
Edwards et al. Antigenic heterogeneity of breast cell lines detected by monoclonal antibodies and its relationship with the cell cycle. Journal of cell science. Feb. 1, 1985;73(1):321-33.
Fell et al. Homologous recombination in hybridoma cells; heavy chain chimeric antibody produced by gene targeting. Proceedings of the National Academy of Sciences. Nov. 1, 1989;86(21):8507-11.
Garrigues et al. Detection of a human melanoma-associated antigen, p97, in histological sections of primary human melanomas. International Journal of Cancer. May 15, 1982;29(5):511-5.
Huang, et al. (2009) Immunotherapy 2(2): 1-18.
Huston et al. Protein engineering of antibody binding sites: recovery of specific activity in an anti-digoxin single-chain Fv analogue produced in *Escherichia coli*. Proceedings of the National Academy of Sciences, Aug. 1, 1988;85(16):5879-83.
Jaffers et al. Anti-Idiotypic and Non-Anti-Indiotypic Antibodies to OKT3 Arising Despite Intense Immunosuppression. Transplantation. May 1, 1986;41(5):572-8.
Jin et al. Characterization of a murine-human chimeric antibody with specificity for the pre-S2 surface antigen of hepatitis B virus expressed in baculovirus-infected insect cells. Virus research. Oct. 31, 1995;38(2):269-77.
Jurcic, Joseph G., et al. "Monoclonal antibody therapy of cancer", Cancer Chemotherapy and Biological Response Modifiers Annual 17, Chapter 10, Elsevier Science B.V., pp. 195-216 (1997).
Kajiji et al. Six monoclonal antibodies to human pancreatic cancer antigens. Cancer research. Mar. 1, 1987;47(5):1367-76.
Köhler et al. Continuous cultures of fused cells secreting antibody of predefined specificity, nature. Aug. 1975;256:495-7.
Kozbor et al. The production of monoclonal antibodies from human lymphocytes. Immunology Today. Mar. 1, 1983;4(3):72-9.
Lazar et al. Transforming growth factor alpha: mutation of aspartic acid 47 and leucine 48 results in different biological activities. Molecular and Cellular Biology. Mar. 1, 1988;8(3):1247-52.
Lee et al. Generation and characterization of a novel single-gene-encoded single-chain immunoglobulin molecule with antigen binding activity and effector functions. Molecular immunology. Jan. 31, 1999:36(1):61-71.
Metzger, et al. (1982) Cancer Research 42(2): 601-608.
Miller at al. Monoclonal antibody therapeutic trials in seven patients with T-cell lymphoma. Blood. Nov. 1, 1983;62(5):988-95.
Morrison et al. Chimeric human antibody molecules; mouse antigen-binding domains with human constant region domains. Proceedings of the National Academy of Sciences. Nov. 1, 1984;81(21):6851-5.
Nakao et al. Clinical application of a new monoclonal antibody (1987) against PIVKA-II in the diagnosis of hepatocellular carcinoma and pancreatobiliary malignancies. American Journal of Gastroenterology, Jun. 1, 1997;92(6).
Neuberger et al. Recombinant antibodies possessing novel effector functions. Nature. Dec. 1983:312(5995):604-8.
Padlan EA. Anatomy of the antibody molecule. Molecular immunology. Feb. 1, 1994;31(3):169-217.
Pancreas Cancer Web, hosted at URL: http://www.path.jhu.edu/pancreas/, Copyright © 2006 The Johns Hopkins University, Baltimore, Maryland, Last Modified: May 12, 2006.
Remington's Pharmaceutical Science, 16th ed., Mack Publishing Co., Easton, PA., 1980.
Rousseaux et al. Optimal conditions for the preparation of proteolytic fragments from monoclonal IgG of different rat IgG subclasses. Methods in enzymology. Dec. 1985;121:663-9.
Rudikoff et al. Single ammo acid substitution altering antigen-binding specificity. Proceedings of the National Academy of Sciences. Mar. 1, 1982;79(6):1979-83.
Ryu et al. A humanized antibody with specificity for hepatitis B surface antigen. Human Antibodies. Jan. 1, 1996;7(3):113-22.
Sakamoto, et al. (2000) Cancer Chemother. Pharmacol. 46(Suppl.): S27-S32.
Sambrook, et al. (1989) Molecular Cloning: A Laboratory Manual, Cold Spring Harbor Laboratory Press, Cold Spring Harbor, NY. (Table of Contents).
Schroff et al. Human anti-murine immunoglobulin responses in patients receiving monoclonal antibody therapy. Cancer Research. Feb. 1, 1985;45(2):879-85.
Simons et al. Bioactivity of autologous irradiated renal cell carcinoma vaccines generated by ex vivo granulocyte-macrophage colony-stimulating factor gene transfer. Cancer Research. Apr. 15, 1997;57(8):1537-46.
Sung et al. Natural killer (NK) cells as effectors of antibody-dependent cytotoxicity with chimeric antibodies reactive with human squamous-cell carcinomas of the head and neck. International journal of cancer. Jun. 9, 1995;61(6):864-72.
Takeda et al. Construction of chimaeric processed immunoglobulin genes containing mouse variable and human constant region sequences. Nature. Dec. 1984;314(8010):452-4.
Ward et al. Binding activities of a repertoire of single immunoglobulin variable domains secreted from *Escherichia coli*. Nature. Oct. 12, 1989;341(6242):544-6.
Yazaki et al. Humanization of the anti-CEA T84. 66 antibody based on crystal structure data. Protein Engineering Design and Selection. May 1, 2004;17(5):481-9.
George et al. "Differential Effects of Anti-β2-Glycoprotein I Antibodies on Endothelial Cells and on the Manifestations of Experimental Antiphospholipid Syndrome." Circulation. Mar. 10, 1998;97(9):900-6.
Vajdos et al. "Comprehensive functional maps of the antigen-binding site of an anti-ErbB2 antibody obtained with shotgun scanning mutagenesis." Journal of molecular biology. Jul. 5, 2002;320(2):415-28.

(56) References Cited

OTHER PUBLICATIONS

Brown et al. "Tolerance of single, but not multiple, amino acid replacements in antibody VH CDR 2: a means of minimizing B cell wastage from somatic hypermutation?." The Journal of Immunology. May 1, 1996;156(9):3285-91.

* cited by examiner

CMV promotor: bases 209-863

T7 promotor: bases 864-882

Polylinker: bases 889-994
Sp6 promotor: bases 999-1016

BGH poly A: bases 1018-1249

SV40 promotor: bases 1790-2115
SV40 origin of replication: bases 1984-2069

Neo$^R$ORF: bases 2151-2932

SV40 poly A: bases 3120-3250 pUC19 backbone: bases 3272-5446

Amp$^R$ORF: bases 4450-5310

SruI – PvuII – ligated into BsmI

V1.1-130923sa

The Chi31.1 light chain gene has been inserted at BamHI and XbaI sites of the vector pDCM-dhfr.

The Chi31.1 heavy chain gene has been inserted at EcoRI and NotI sites of the vector pDCM-dhfr.

Figure 2. Translated DNA sequence of the Light chain variable region of Chi31.1.

```
         10        20        30        40        50        60        70        80        90       100       110       120
          *         *         *         *         *         *         *         *         *         *         *         *
ATGAAGTCACAGACCCAGGTCTTGGTATTTCTACTGCTGTGGTTGTCTGGTGTCCATGGAGTATGTGACCCAGACTCCACTCTCCCTGTCTGTCACCATTGGAGACCAGGGTTACC
TACTTCAGTTGTCTGGGTCAGAAGCCATAAAGATGAGAGACACACAGAGAGTCCCCTCATAACTACTGGGTCTGAGCGTTTAAGGACGAACATAGTGTCTCGTGTCCAATGG
MetLysSerGlnThrGlnValPheLeuLeuLeuCysValSerGlyAlaHisGly|SerIleValMetThrGlnThrProLysPheLeuLeuValSerAlaGlyAspArgValThr>
                                                     mature
         130       140       150       160       170       180       190       200       210       220       230       240
          *         *         *         *         *         *         *         *         *         *         *         *
ATAACCTGCAAGGCCAGTGAGAGTGTGAGTAATGATGTAGCTTGTACCAACAGAAACAGGGCAGTCTCTAAACTGCTGATATCATCAATGCTACACTGGAGTCCTGAT
TATTGGAGGTTCCGGTCAGTCAGTTGATCCACTCATTACTACATGAAACCATGGTGTCTTTGTCCCGTCAGAGGATTTGACGACTATATGATAGGGTTAGGGTTAGCGTCAGGGACTA
IleThrCysLysAlaSerGlnSerValSerAsnAspValAlaTrpTyrGlnGlnLysProGlyGlnSerProLysLeuLeuIleTyrTyrAlaSerAsnArgTyrThrGlyValProAsp>
         250       260       270       280       290       300       310       320       330       340       350       360
          *         *         *         *         *         *         *         *         *         *         *         *
CGCTTCACTGGCAGTGGATATGGACGGATTTCACTTCACCATCAGCACTGCAGGCTGAAGACCTGGCAGTTTATTCTGTCAGCAGGATTATAGCTCTCCGCTCACGTTCGGTGCT
GGAAGTGACGGTCACCTATACCTGCCTAAAGTGAAGTGGTAGTCGTACTTCTGACACGTCCGACTTCTGACGTGGAGCAGCCCTAATATAAAGACAGCAGCCAGTCCAAGCCACGA
ArgPheThrGlySerGlyTyrGlyThrGlyThrAspPheThrPheThrIleSerThrValGlnAlaGluAspLeuAlaValTyrPheCysGlnGlnAspTyrSerSerProLeuThrPheGlyAla>
         370       380
          *         *
GGGACCAAGCTGGAGCTGAAACGT
CCCTGGTTCGACCTCGACTTTGCA
GlyThrLysLeuGluLeuLysArg>
```

FIG. 2

FIG. 3

31.lLv Map (1 > 387) 268 Cut Sites    Site Summary by Enzyme

Non-Cutting Enzymes

| | | | | |
|---|---|---|---|---|
| Aac I | Aat II | Aca I | Acc I | AccEBI |
| Ace II | Acs137 I | Adel | Afa24R I | Age I |
| Ait II | Alw I | AlwN I | AlwN I | Apa I |
| ApaL I | Apu16 I | Aqu I | Ama I | Asp52 I |
| Asp748 I | Ate I | AtuC I | Asel | Bae I |
| BamH I | Ban II | Bbe I | Avr II | Bbv I |
| Bce83 I | Bav I | Bcg I | Bbf7411 I | Bcn I |
| Bco63 I | BceF I | Bep I | Bcl VI | Bfm I |
| Bgl II | Bcu I | Bma I | Bfi89 I | Bmr I |
| Bpl I | Blp I | BsL I | Bme142 I | BsaB I |
| Bsak I | Bli49 I | BsaW I | BmeT I | BscG I |
| BseM I | Bpu1268 I | BsaW I | Bsa0 I | BsmH I |
| BseR I | BsaU I | Bsi SI | Bsc107 I | Bsp87 I |
| Bso J | BshL I | BsiSI | BsmB I | BsrG I |
| BspC I | Bsp120 I | Bsp19 I | Bsp24 I | Bst295 I |
| BspF I | BspLU11 I | Bsr0 I | BsrE I | BstZ2 I |
| BssH II | BspLU11 II | Bs1473 I | Bst29 I | CfrA I |
| Bst98 I | Bst1107 I | BstU I | Bst224 I | Drd I |
| BstaP I | BstHP I | Cfr10 I | BstX I | Ecl 137 I |
| BsuM I | CciN I | Dde I | Cfr14 I | Eco88 I |
| BsuE II | Csp I | Ecl I | Dra III | EcoK I |
| Chu II | Eae I | Ear I | Eci EI | EcoV III |
| Cla I | Eco31 I | Eco47 III | Eco72 I | Fsp I |
| Dsa I | Eco24 I | EcoDR2 | EcoE I | Hin2 I |
| Dsa VI | EcoD XXI | EcoR124 I | EcoRD2 | Hsp92 I |
| Eco1831 I | EcoR V | Fau I | Fnu4H I | Mlu1106 I |
| EcoB I | Esp3 I | Hae II | HgiE II | MthZ I |
| EcoD I | Hae II | Hund III | Hpa I | Nhe I |
| EcoR I | Hinc II | Hind III | Mja I | PinA I |
| Eco01109 I | M. CviBIII | M.Phi3TII | MspA1 I | Pst 1 |
| Ehe I | Msc I | Msl I | Nde I | SanD 1 |
| Gdi II | Nci I | Nco I | Pf11108 I | Sfi I |
| HinJC I | Nsp I | Pac I | PspA I | Srf I |
| HinP1 I | Ppu6 I | PpuM I | Sac II | StySJ |
| Lsp1270 I | RleA I | Rrh4273 I | SexA I | Tat I |
| M. BbvS I | Sci I | Sdi I | Spe I | Uba1221 I |
| Mme I | Sml I | Sna I | Sty I | Xcm I |
| Mnl I | Ssp I | Sst I | Taq I | |
| Nae I | Swa I | Stu I | Tsp32 I | |
| Nar I | Tru9 I | Syn II | Tth111 I | |
| Not I | UbaD I | Tse I | Vsp I | |
| Nru I | Xma III | UbaE I | | |
| Ppe I | | Xmn I | | |
| Ppu1253 I | | | | |
| Pvu II | | | | |
| Rhc I | | | | |
| Sca I | | | | |
| SauLP I | | | | |
| SgrA I | | | | |
| Sma I | | | | |
| Sse8647 I | | | | |
| Sso I | | | | |
| StySP I | | | | |
| Sty SO | | | | |
| Tfi I | | | | |
| Uba1326 I | | | | |
| Uba1282 I | | | | |
| Xho II | | | | |
| Xma I | | | | |

(Second column header: Acc III, Afl IV, Aos III, Asp1 I, Bae I, Bbr I, Bcl I, Bfi I, Bmg I, BsoA I, BscE I, BsmG I, Bsp24 I, BsrF I, Bst29 I, BstZ I, Cfr91, Dra III, EciE I, Eco82 I, EcoCR I, EcoRD3, Fse I, Hha I, Hpa II, Mlu I, Mspi, NgoM I, Pfu I, Pss I, Sal I, Sfc I, Sph I, StyLT III, Taq II, Uba1220 I, Xba 1)

(Fifth column: Ace I, Ahya I, ApaB I, Asp5H I, Bal I, Bca I, Bco163 I, Bgl I, Bna I, Bsaf I, BscJ I, BsoD I, BspD I, BsrW I, Bst71 I, Bsu36 I, CfrJ41, Drd I, EclHK I, EcoA I, EcoN I, Ecoprr I, Fsu I, Hin8 I, Kas I, Mlu113 I, Mun I, Nll387/7 I, Pme I, Pvu I, Sap I, Sgf I, Sse8387 I, StySK1, Tau I, Uba1303 I, Xha I)

Figure 4. Translated DNA sequence of the Heavy chain variable region of Chi31.1.

```
         10        20        30        40        50        60        70        80        90       100       110       120
          *         *         *         *         *         *         *         *         *         *         *         *
ATGGCTTGGGTGTGGACCTTGCTATTCCTGATGCCAGTCGTCAACAAGTGCCAAGCACAGATCCAGTTGGTGCAGTCTGGACCTGAGCTGAAGAAGCCTGAGAGACAGTCAAGATCTC
 MetAlaTrpValTrpThrLeuLeuPheLeuMetAlaAlaAlaGlnSerGlyProGluLeuLysLysProGluArgGlnSerLysSer>

130       140       150       160       170       180       190       200       210       220       230       240
          *         *         *         *         *         *         *         *         *         *         *         *
TGCAAGGCTTCTGGTATACCTTCACAAACTATGGAATGAACTGGGTGAAGCAGGCTCCAGGAAAGGGTTTAAAGTGGATGGGCTGGATAAACACCTACACTGAGAGGCCAACATATGCT 250       260       270       280       290       300       310       320       330       340       350       360
          *         *         *         *         *         *         *         *         *         *         *         *
ACGTTCCGAAGACCCATATGAAGTGTTTGATACCTTACTTGACCCACTTCGTCGGAGGTCCTTTCCCAAATTTCACCTACCGACTATTTGTGAGTGACCTCTGGTGTATACGA 370       380       390       400       410
          *         *         *         *         *
GGTAAATACTTTGACTACTGGGGCCAAGGCACCACTCTCACAGTCTCCTCA
```

FIG. 4

31.1Hv Map (1 > 411) 280 Cut Sites   Site Summary by Enzyme

Non-Cutting Enzymes

| | | | | | |
|---|---|---|---|---|---|
| Aac I | Aaq I | Aat II | Aca I | Aco III | Acc65 I | AccEBI | Ace II |
| Acl I | Acr I | Acs1371 I | Acs I | Adel | Afl III | Afl IV | Age I |
| AhyA I | Ain I | Alw44 I | AlwN I | Ama I | Apa I | ApaB I | ApaL I |
| Ape I | Apo I | Apu16 I | Aqu I | Asc I | Asp I | Asp16H I | Asp52 I |
| Asp5H I | Asp748 I | Asp78 I | Ate I | Ase I | Ava III | Avr II | Bae I |
| Bae I | Bal I | BamH I | AtuC I | Ava I | Bbf7411 I | Bbr I | Bbs I |
| Bca I | Bce83 I | BceF I | Bbe I | BbeA I | Bcl I | Bcn I | Bco102 II |
| Bco163 I | Bco63 I | Bct I | Bcef I | Bcg I | Bfi89 I | Bfm I | BfrB I |
| Bgl I | Bli49 I | Blp I | Bcu I | Bfa I | Bna I | Bpl I | Bpu1268 I |
| Bsa I | BsaO I | BsaA I | Bma I | BmeT I | BsaK I | BsaM I | BsaW I |
| Bsb I | BscA I | BscE I | BsaB I | BsaF I | Bse59 I | BseR I | BshL I |
| BsiHKA I | BsiS I | BsiW I | BscG I | BscJ I | BsmG I | BsmN I | BsoD I |
| BsoJ I | Bsp117 I | Bsp120 I | BsmB I | BsmE I | Bsp24 I | Bsp87 I | BspD I |
| BspH I | BspJ106 I | BspLU11 I | Bsp19 I | Bsp21 I | BspST5 I | BsrO I | BsrF I |
| BsrG I | BssH II | BssS I | BspLU11 II | BspM I | Bst98 I | BstE II | BstHP I |
| BstU I | BstX I | BstZ11 I | Bst1473 I | Bst29 I | BsuM I | CciN I | Cfo I |
| Cfr10 I | Cfr9 I | CfrA I | BstZ2 I | Bsu36 I | Cla I | Csp I | Csp45 I |
| Csp6 I | CviA II | CviC I | CviR II | Dra III | Drd II | Dsa I | Eae I |
| Ecal | Eci I | EciA I | EciE I | Ecl137 I | Eco1831 I | Eco24 I | Eco3II |
| Eco47 III | Eco52 I | Eco72 I | EcoB2 I | Eco881 | EcoB I | EcoO I | EcoD XXI |
| EcoDR2 | EcoDR3 | EcolCR I | EcoK I | EcoN I | EcoP I | EcoP15 I | EcoR I |
| EcoR V | EcoR124 I | EcoR124 II | EcoRD2 | EcoRD3 | EcoVIII | Eco0109 I | Esp16 I |
| Esp3 I | Fau I | Fse I | Fsp I | Fsu I | Gdi II | Ehe I | Hal I |
| Hga I | HgiE II | Hho I | Hha I I | Hin2 I | Hin8 II | Hae II | HinP I I |
| Hinc II | Hind III | Hine I | Hinf I | Hpa I | Hsp92 I | HinJC I | Kpn I |
| Lsp170 I | Mlu I | M. CcrM I | M. CviB III | M. Phi3T II | Mae III | Kas I | Mbi I |
| Mja I | Msp I | Mlu1106 I | Mlu1113 I | Mly I | Msc I | Mbi I | Mfe I |
| Msp I | Mth Z I | Mun I | Nae I | Nar I | Nco I | Msl I | Msp20 I |
| Nla III | Nli3877 I | Not I | Nru I | Nsi I | Nsp I | NgoM I | Nhe I |
| Pfu I | PinA I | Ple I | Pme I | Ppe I | Ppu10 I | Pac I | Pfl1108 I |
| PshA I | Psp1406 I | PspA I | Pss I | Pst I | Pvu I | Ppu1253 I | PpuM I |
| Rsa I | Sac I | Sac II | Sal I | SanD I | Sap I | Rhc I | Rrh4273 I |
| Sdi I | Sel I | SexA I | StaN I | Sfc I | Sfi I | SauLP I | Sca I |
| Sma I | Smi I | SnaB I | Spe I | Sph I | Srf I | Sgf I | SgrA I |
| Swo I | Ssp I | Sst I | Stu I | StyLT III | StySJ | Sse8387 I | Sse8647 I |
| TseC I | Syn II | Tai I | Taq I | Taq II | Tat I | StySK I | StySP I |
| Uba1303 I | Tsp32 I | Tsp45 I | Tsp509 I | Tth111 I | Tth111 II | Tau I | Tfi I |
| Xho I | Uba1326 I | Uba1382 I | UbaD I | UbaE I | Van91 I | Ttm I | StySO |
| | Xma I | Xma III | Xmn I | | | Vsp I | Tfl I |
| | | | | | | Uba1220 I | Uba1221 I |
| | | | | | | Xba I | Xcm I |

FIG. 5

MONOCLONAL ANTIBODY THERAPY FOR PANCREAS CANCER

CROSS-REFERENCE TO RELATED APPLICATIONS

This application is a divisional of U.S. patent application Ser. No. 15/417,326, filed Jan. 27, 2017, which is a divisional of U.S. patent application Ser. No. 14/509,428, filed Oct. 8, 2014, now U.S. Pat. No. 9,592,290, which is a divisional of U.S. patent application Ser. No. 13/011,631, filed Jan. 21, 2011, now U.S. Pat. No. 9,034,588, which is a divisional of U.S. patent application Ser. No. 11/234,645, filed Sep. 22, 2005, now abandoned, which is a continuation of U.S. patent application Ser. No. 10/472,008, filed Sep. 15, 2003, now abandoned, which is a national stage entry of International Pat. Appl. No. PCT/US2002.1009193, filed Mar. 15, 2002, which claims the benefit of U.S. Provisional Appl. No. 60/276,284, filed Mar. 15, 2001, the disclosures of each of which are hereby incorporated by reference in their entireties.

SEQUENCE DISCLOSURE

This application includes as part of its disclosure a biological sequence listing which is being concurrently submitted through EFS-Web. Said biological sequence listing is contained in a file named "43282o2408.txt" which was created Oct. 17, 2018, and has a size of 6,316 bytes, and is hereby incorporated by reference in its entirety.

1. INTRODUCTION

The present invention relates to the use of monoclonal antibody 31.1 and its equivalents and co-specific antibodies in the treatment of pancreas cancer. It is based, at least in part, on the discovery that monoclonal antibody 31.1 is reactive with malignant, but not non-malignant, pancreatic cells. The present invention further provides polynucleotide and amino acid sequences comprising the light chain variable region and heavy chain variable region of Mu-31.1 as set forth in FIG. 2 and FIG. 4, respectively. Such polynucleotide sequences may be used to recombinantly express 31.1 equivalent antibodies for use in the methods of the invention.

2. BACKGROUND OF THE INVENTION

2.1. Pancreas Cancer

Pancreas cancer is the fifth leading cause of cancer death in the United States, with approximately 28,000 Americans expected to die from the disease this year (Pancreas Cancer Web, The Johns Hopkins Medical Institutions, http://162.129.103.69: 80/PANCREAS-INTRO). At present, the only potentially curative treatment is surgical removal of the cancer, in the context of an extensive and complex procedure which removes the head, neck and uncinate process of the pancreas as well as the majority of the duodenum (the "Whipple operation"). Without treatment, the overall 5 year survival rate is only 3 percent (Id.).

Chemotherapy (often using gemcitabine (Gemzar®)) and radiation therapy are the main treatments offered to patients with unresectable tumors (Id.). An experimental immunotherapy is currently being studied in which a patient's own cells are genetically modified to express the immune stimulatory protein, granulocyte macrophage colony stimulating factor, irradiated to prevent tumor growth, and then reintroduced into the patient, where they will hopefully stimulate an immune response (1997, Cancer Res. 57: 1537-1546; Pancreas Cancer Web, The Johns Hopkins Medical Institutions, http://162.129.103.69:80/PANCREAS_MEDICAL_TX)).

2.2. Monoclonal Antibody 31.1

Antibody 31.1 represents a protein-directed monoclonal antibody derived by immunizing BALB(c) mice with a preparation of membrane obtained from pooled (human) allogeneic colon carcinoma specimens. The cells used to prepare the antigen were fragmented using a nitrogen (Parr) bomb and then subjected to ultracentrifugation. Membrane material was initially tested by electron microscopy to guarantee consistency from batch to batch, ruling out cytoplasmic and nuclear components. It was then sonicated and fractionated with sephadex G200. Discontinuous polyacrylamide gel electrophoresis was used for the initial partial purification (approximately 80%) and 30 μgm tested for delayed cutaneous hypersensitivity (DHR), (3). BALB mice were immunized by intraperitoneal injection of 50 micrograms of colon carcinoma associated antigen. A second injection was given 10 days later and the mice then sacrificed to obtain spleen cells for fusion. Fusion was performed by incubating $5 \times 10^7$ mouse spleen cells with $10^7$ sp2/0-AG 14 myeloma cells in 40% PEG. The antigen defined by the monoclonal antibody 31.1 has been shown to have M.W. of 72,000. Studies using immunoperoxidase have suggested that the antigen recognized by 31.1 is seen with greater frequency in the higher grade colon tumors. Specificity for the antibody is high, so that in a study of shed colonocytes at the Mayo Clinic, sensitivity and specificity were superior when compared with anti-CEA, anti-MUC1 and B72.3.

Several candidate antibodies were isolated and tested from the 1st generation TAA. All proved to be protein derived and relatively specific for colon carcinoma. Antibody 31.1 corresponded to one of the two antigens that have been shown to migrate closely on gel-electrophoresis and related to the immunogenic glycoprotein inducing the DHR. The murine version is of IgG2a isotype which converts to an IgG1 isotype on chimerization. 31.1 was found to have strong localization indices. As such, this antibody was the first to be chimerized.

For chimerization of monoclonal antibody 31.1, the protein coding exon of 31.1 heavy chain variable region gene was spliced to the protein coding exons of human gamma 1 chain constant region. PCR was employed. The 31.1 VH cDNA was amplified by the PCR using the degenerate backward primers synthesized based on the consensus first framework (FR1) region DNA sequences and a forward primer synthesized according to the consensus J-C junction region DNA sequences. The amplified 31.1 $V_H$ DNA was cloned into the pBluescript vector and sequenced. Chimeric 31.1 was produced by transfecting SP2/0 AG14 cells with the vector.

Monoclonal antibody 31.1 and a chimeric (humanized) version of that antibody are described in U.S. Pat. No. 5,688,657 issued Nov. 18, 1997, now the subject of a reissue application, the contents of which are hereby incorporated by reference in its entirety herein. Furthermore, monoclonal antibody 31.1 has been deposited with the American Type Culture Collection ("ATCC"), having an address at 10801 University Blvd., Manassas, Va., 20110-2209 and assigned accession number ATCC PTA-2497 and the chimerized version has been deposited with the ATCC and assigned accession number 12316.

3. SUMMARY OF THE INVENTION

The present invention relates to the use of binding equivalents of monoclonal antibody 31.1, including chimerized and/or humanized versions thereof, antibody fragments and competitively binding antibodies and antibody fragments, as well as co-specific antibodies, derivatives and fragments in the treatment of pancreas cancer.

It is based, at least in part, on in vitro studies using both murine and chimeric versions of 31.1 which compared the ADCC activites of the 31.1 antibodies with D6-12 and 17.1a (Panorex). While the murine version of 31.1 can induce a 35% ADCC response, the chimeric version has been shown to result in 80% of tumor cells being destroyed every three hours, using a chromium release assay. This compares with a 30% rate of destruction associated with D6-12 and a 15% rate for Panorex. Using xenograft models with human colon cancer cell lines LC-174T and Colo205, chimeric 31.1 was found to cause regression of established tumor lines (well defined molecules) after inoculating two million tumor cells into the hind legs of nude mice and administering intraperitoneal antibody at 10 days along with human effector cells. At 30 days the volume of tumor in the treated animals when compared to controls was reduced by more than 95%. Similar results may be expected when the antibody is directed toward pancreatic cancer cells, as the 31.1 antibody has been shown to bind to antigen present in pancreatic cancer cells, but not non-malignant pancreatic tissues.

The present invention provides polynucleotide and amino acid sequences comprising the light chain variable region and heavy chain variable region of Mu-31.1 which may be used to express chimerized 31.1 antibodies. The nucleotide sequences of the invention include: (a) the nucleotide sequences shown in FIG. 2 (SEQ ID NOS:1 and 2) or FIG. 4 (SEQ ID NOS:4 and 5); (b) a nucleotide sequence (SEQ ID NOS:1 and 4) that encodes the amino acid sequence shown in FIG. 2 (SEQ ID NO:3) or FIG. 4 (SEQ ID NO:6); and (c) any nucleotide sequence that (i) binds to the nucleotide sequence of FIG. 2 or FIG. 4 under stringent hybridization conditions, e. g., hybridization to filter bound DNA in 0.5 M NaHPO$_4$, 7% sodium dodecyl sulfate (SDS), 1 mM EDTA at 65° C., and washing in 0.1×SSC/0.1% SDS at 68° C. and (ii) encodes for a light and heavy chain variable region capable of binding with the same immunospecificity as the chimeric 31.1 monoclonal antibody.

The invention further provides for a new expression construct of chimerized 31.1 antibody, termed pRc/CMV31.1 which has been deposited with the ATCC and assigned accession no. ATCC [ ]. This plasmid carries a dihydrofolate reductase ("dhfr") expression unit driven by an enhancer-deficient SV40 early promoter that allows expression at greater than 200 mg/liter in dihydrofolate reductase deficient Chinese hamster ovary cells.

4. BRIEF DESCRIPTION OF THE DRAWINGS

Figure 1C:
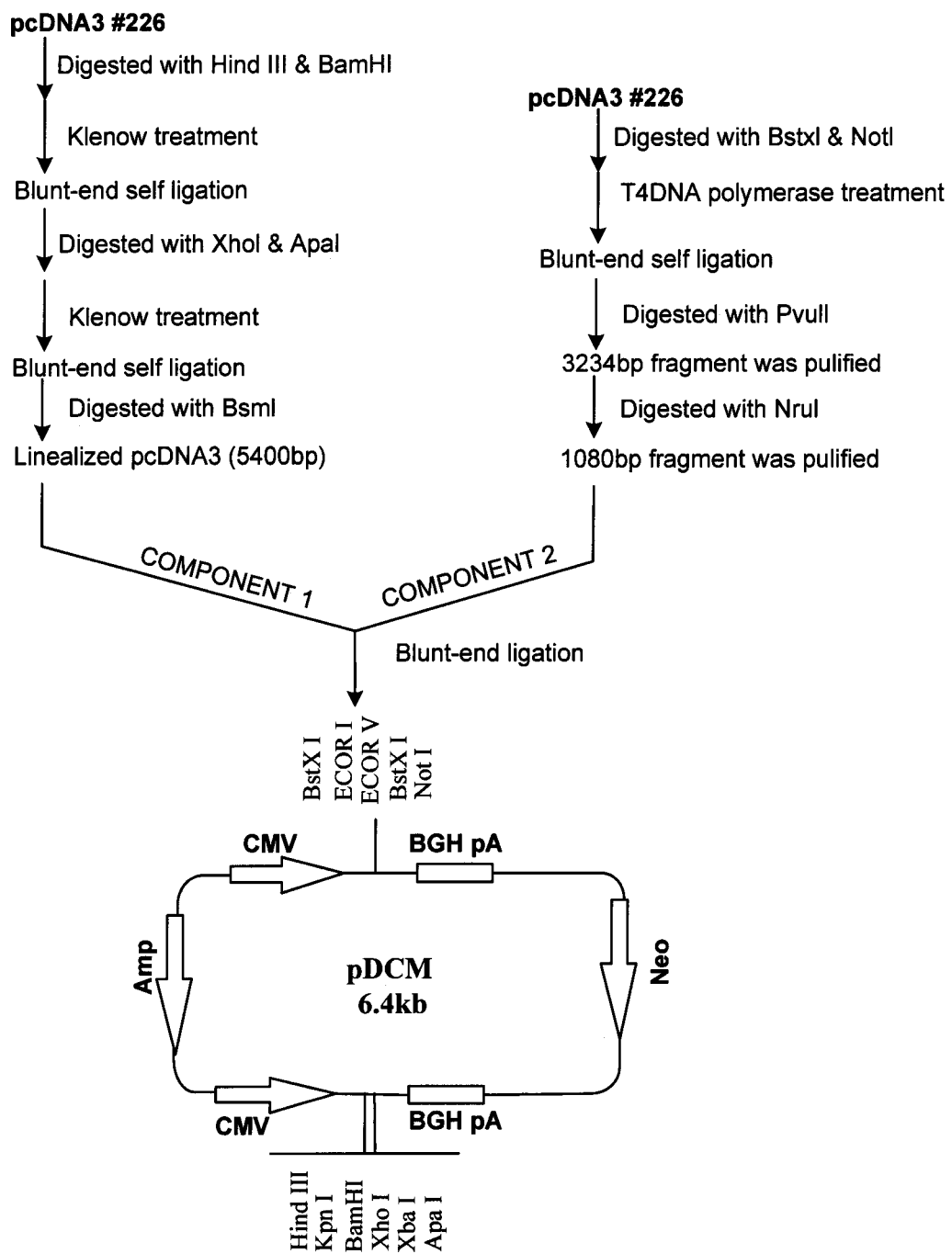
Figure 1D:
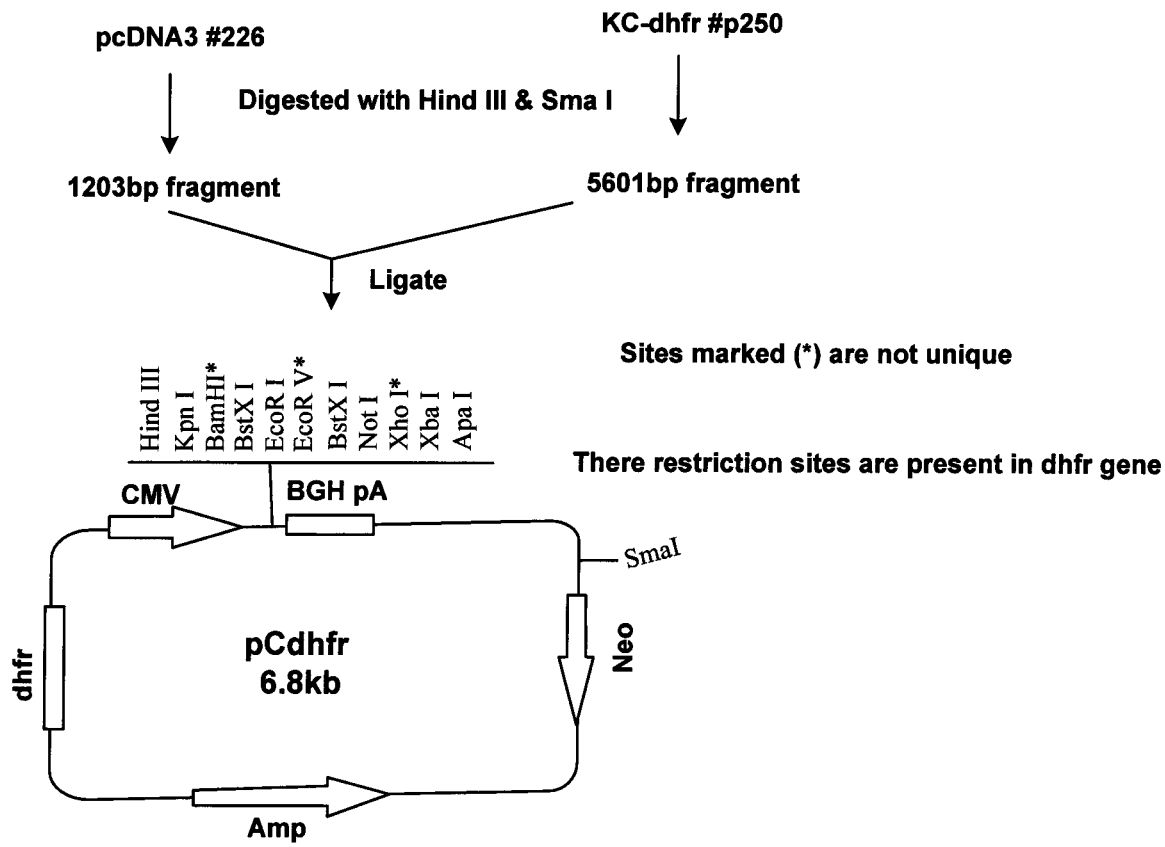
Figure 1E:
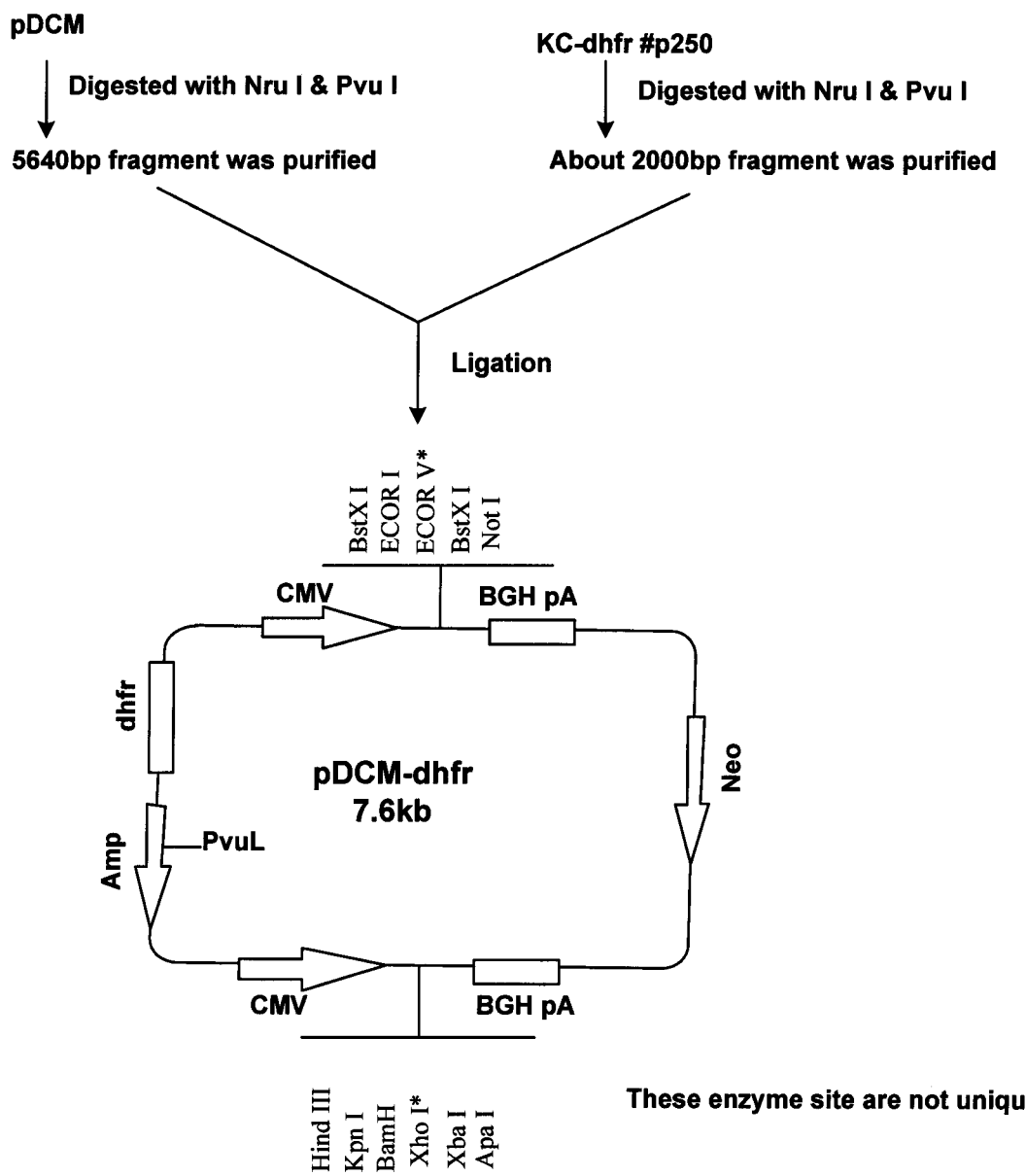
Figure 1F:
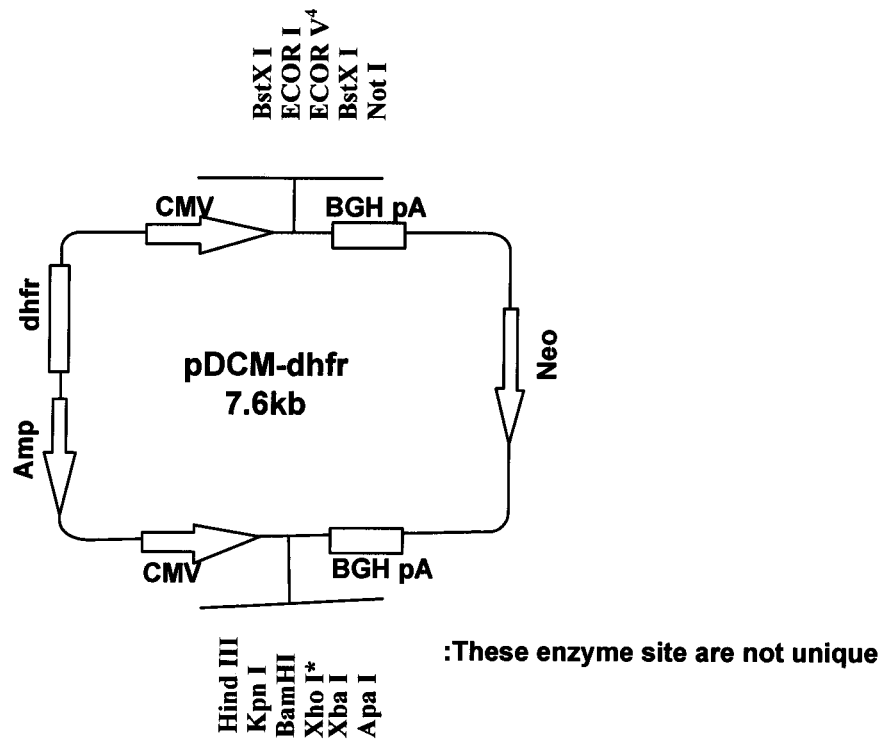

FIG. 1A-F. Series of plasmids used to construct pRc/CMV 31.1 vector by inserting the Chi31.1-1 light chain and heavy chain genes into plasmid pDCM-dhfr (FIG. 1F).

FIG. 2. Nucleic acid sequence (double stranded, SEQ ID NOS:1 and 2) and possible amino acid sequences (depending on reading frame, SEQ ID NO:3) of the 31.1 light chain variable region, showing restriction enzyme cleavage sites.

FIG. 3. List of non-cutting enzymes of the light chain variable region nucleic acid sequence shown in FIG. 2.

FIG. 4. Nucleic acid sequence (double stranded, SEQ ID NOS:4 and 5) and possible amino acid sequences (depending on reading frame, SEQ ID NO:6) of the 31.1 heavy chain variable region, showing restriction enzyme cleavage sites.

FIG. 5. List of non-cutting enzymes of the heavy chain variable region nucleic acid sequence shown in FIG. 4.

Figure 6A:
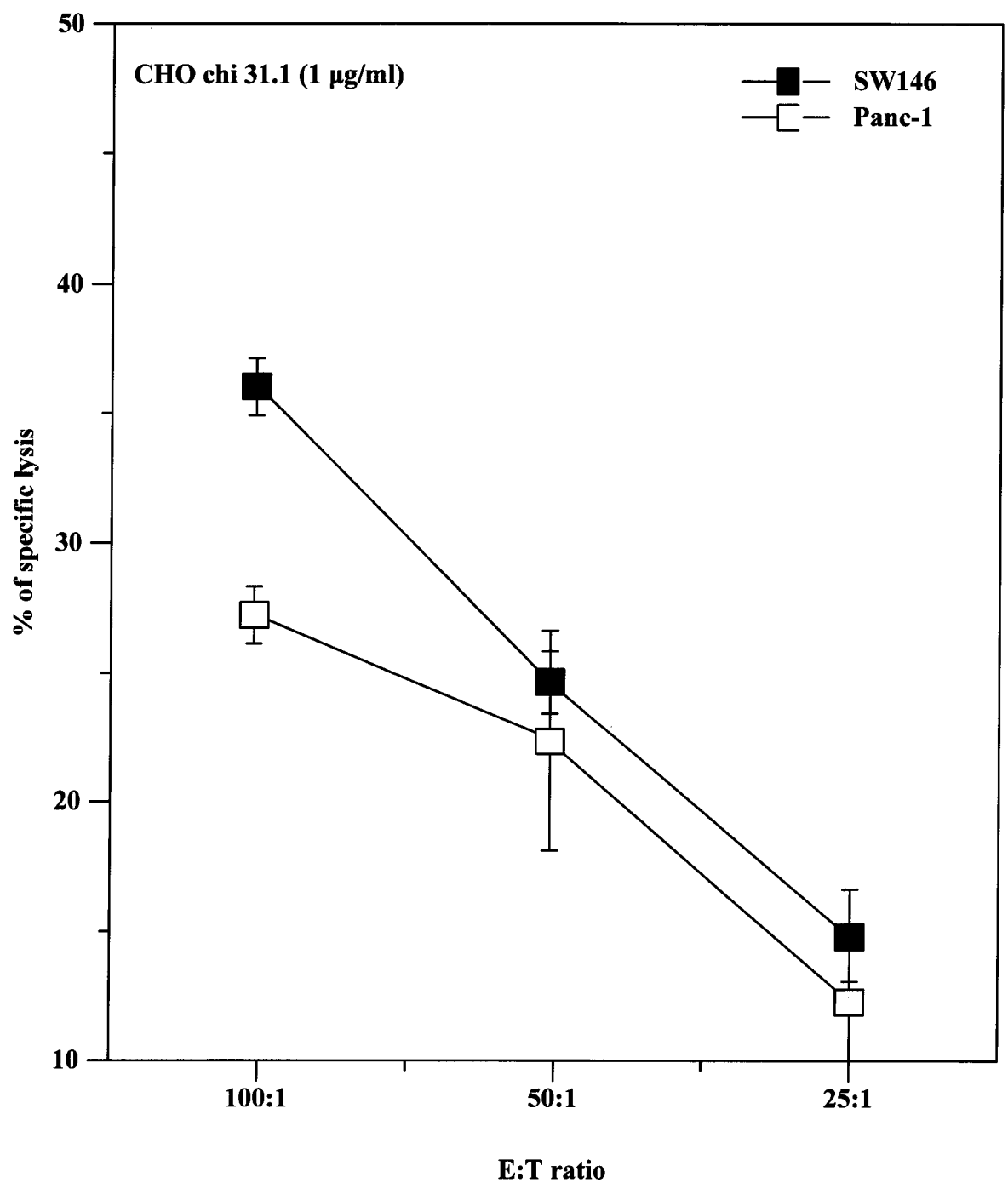
Figure 6B:
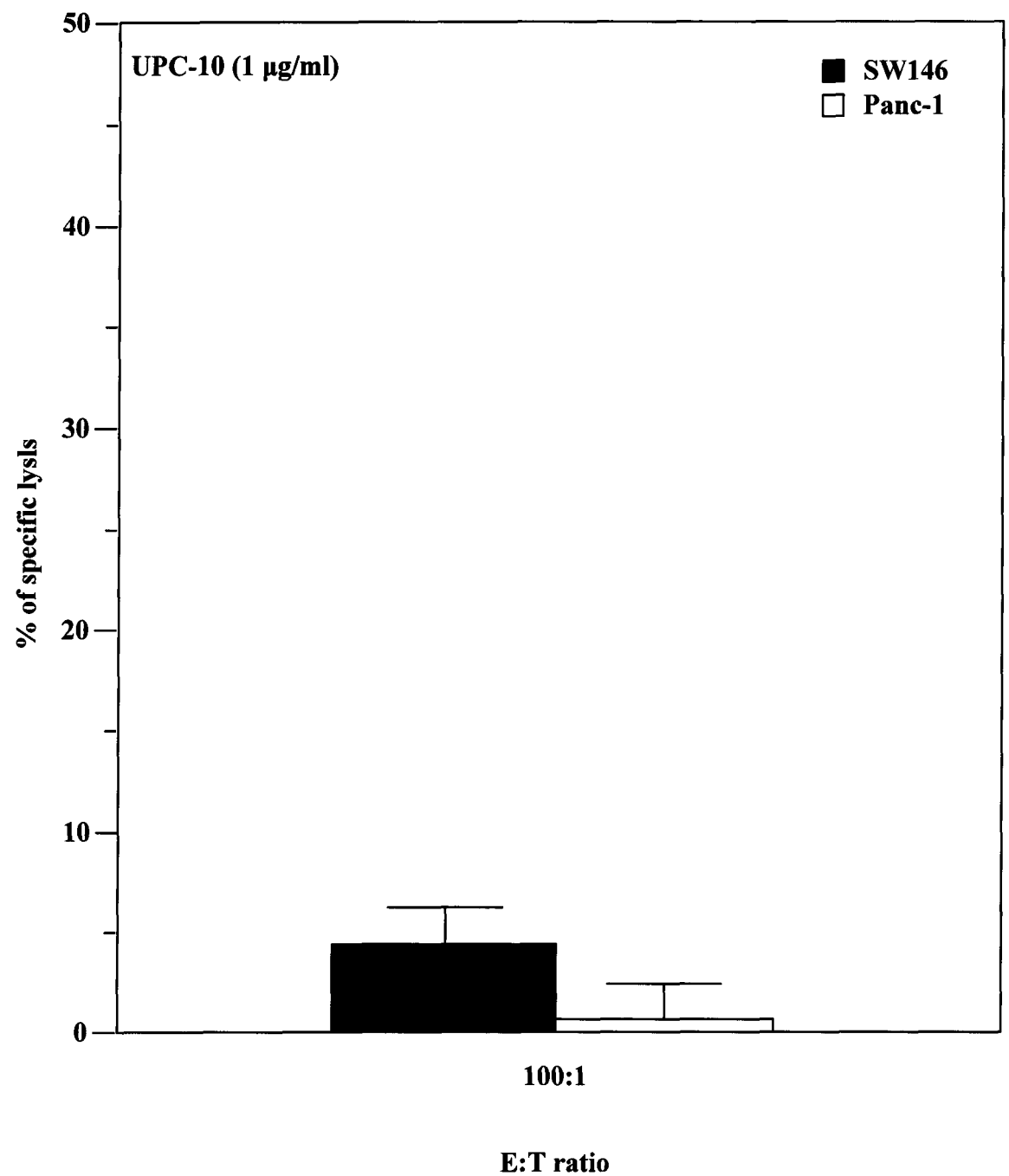

FIG. 6A-B. An antibody-dependent cellular cytotoxicity (ADCC) assay was conducted to test the effector function of the CHO Chi31.1 antibody against target cells SW1643 and PANC-1. As cell lysis occurs in the presence of 31.1 antibody (FIG. 6A) but not in the presence of control antibody (FIG. 6B).

5. DETAILED DESCRIPTION OF THE INVENTION

For purposes of clarity of presentation and not by way of limitation, the detailed description is divided into the following two subsections:
i) monoclonal antibody 31.1 and its equivalents; and
ii) treatment protocol.

5.1. Monoclonal Antibody 31.1 and its Equivalents

Monoclonal antibody 31.1 is a murine monoclonal antibody (hereinafter referred to as Mu-31.1), originally generated by immunization with purified material from colon carcinoma cell membranes. Hybridoma cells secreting this antibody have been deposited with the *American Type Culture Collection* ("ATCC") and assigned accession no. ATCC PTA 2497.

The present invention provides nucleic acid molecules and polypeptides comprising the light chain variable region and heavy chain variable region of Mu-31.1. The nucleotide sequences of the invention include: (a) the DNA sequences shown in FIG. 2 or FIG. 4; (b) a nucleotide sequence that encodes the amino acid sequence shown in FIG. 2 or FIG. 4; (c) any nucleotide sequence that (i) hybridizes to the nucleotide sequence set forth in (a) or (b) under stringent conditions, e. g., hybridization to filter-bound DNA in 0.5 M NaHPO$_4$, 7% sodium dodecyl sulfate (SDS), 1 mM EDTA at 65° C., and washing in 0.1×SSC/0. 1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and (ii) encodes a functionally equivalent gene product. Functional equivalent gene products include those polypeptides which compete with 31.1 for binding to its target antigen. The invention also encompasses nucleotide sequences that encode peptide fragments of the heavy and light chain variable regions, and fusion proteins thereof.

The nucleotides of the invention may be isolated using a variety of different methods known to those skilled in the art. For example, a cDNA library constructed using RNA from cells or tissue known to express the 31.1 monoclonal antibody or its equivalent, can be screened using a labeled nucleic acid probe derived from the sequences depicted in FIG. 2 or FIG. 4. Further, nucleic acid sequences encoding the heavy and light chain variable regions may be derived by performing PCR using two oligonucleotide primers designed on the basis of the nucleotide sequences disclosed herein. The template for the reaction may be cDNA obtained by reverse transcription of mRNA prepared from cell lines or tissue known to express the 31.1. monoclonal antibody.

The invention also encompasses (a) DNA vectors that contain any of the foregoing heavy and light chain variable region sequences and/or their complements (i. e., antisense); (b) DNA expression vectors that contain any of the foregoing heavy and light chain variable region sequences operatively associated with a regulatory element that directs the expression of the heavy and light chain variable region coding sequences; and (c) genetically engineered host cells that contain any of the foregoing heavy and light chain variable region sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

FIG. 2 shows the deduced amino acid sequence of the 31.1 light chain variable region and FIG. 4 shows the deduced amino acid sequence of the 31.1 heavy chain variable region. Thus, the amino acid sequences of the invention include the amino acid sequence shown in FIG. 2 and FIG. 4.

The invention also encompasses proteins that are functionally equivalent to proteins encoded by the nucleotide sequences described above, as judged by any of a number of criteria, including but not limited to the ability to bind to the epitope recognized by the 31.1 monoclonal antibody.

Peptides corresponding to one or more domains of the heavy and light chain variable regions, as well as fusion proteins in which the full length or a portion of the heavy and light chain variable region is fused to an unrelated protein are also within the scope of the invention and can be designed on the basis of the nucleotide and amino acid sequences disclosed herein (see, FIG. 2 and FIG. 4).

While the heavy and light chain variable regions can be chemically synthesized (e. g., see Creighton, 1983, Proteins: Structures and Molecular Principles, W. H. Freeman & Co., N. Y.), the regions may be advantageously produced by recombinant DNA technology using techniques well known in the art for expressing a nucleic acid containing heavy and light chain variable region gene sequences and/or coding sequences. Such methods can be used to construct expression vectors containing the nucleotide sequences described above and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the nucleotide sequences of the invention. Where the heavy and light chain variable regions are expressed as a soluble derivative and are not secreted, the peptide or polypeptide can be recovered from the host cell. Alternatively, where the heavy and light chain variable regions are secreted the peptide or polypeptides may be recovered from the culture media.

The expression systems that may be used for purposes of the invention include but are not limited to microorganisms such as bacteria transformed with recombinant bacteriophage, plasmid or cosmid DNA expression vectors containing nucleotide sequences encoding the 31.1 heavy and light chain variable regions; yeast transformed with recombinant yeast expression vectors containing nucleotide sequences encoding for the 31.1 heavy and light chain variable regions or mammalian cell systems harboring recombinant expression constructs containing promoters derived from the genome of mammalian cells or from mammalian viruses.

Appropriate expression systems can be chosen to ensure that the correct modification, processing and sub-cellular localization of the heavy and light chain variable region protein occurs. To this end, host cells which possess the ability to properly modify and process antibodies for secretion are preferred. For long-term, high yield production of recombinant proteins, such as that desired for development of cell lines for production of chimeric antibodies, stable expression is preferred. Rather than using expression vectors which contain origins of replication, host cells can be transformed with DNA controlled by appropriate expression control elements and a selectable marker gene, i. e., tk, hgprt, dhfr, neo, and hygro gene, to name a few. Following the introduction of the foreign DNA, engineered cells may be allowed to grow for 1-2 days in enriched media, and then switched to a selective media.

A chimeric version of murine 31.1, referred to hereinafter as Chi31.1-1, comprising variable region from Mu-31.1 together with human constant region immunoglobulin sequences, is produced by hybridoma cells deposited with the ATCC and assigned accession no. ATCC CRL-12316.

In a specific embodiment of the invention, a second chimeric version of murine 31.1, hereinafter referred to as Chi31.1-2, having variable regions from Mu-31.1 and human constant immunoglobulin regions and derived from the Chi31.1-1 heavy and light chain genes, may be produced by expression of vector pRc/CMV31.1, described herein, and as shown in FIG. 1. This vector has the advantage of producing high yields of chimeric antibody. A description of the preparation of this vector is provided in the example section, below.

In specific non-limiting embodiments of the invention, further chimeric versions may be produced comprising the variable regions of Mu-31.1. For example, the heavy chain variable region and light chain variable region may be generated using PCR primers designed based on the variable region sequences set forth in FIG. 2 (light chain variable region) and FIG. 4 (heavy chain variable region) or variants thereof to alter the termini to facilitate splicing in a vector of choice and using, as a source of template DNA, DNA collected from a hybridoma that produces a 31.1-Ab equivalent, such as one of the hybridomas set forth above which have been deposited with the ATCC. The variable region encoding sequences may then be combined with human constant-region encoding sequences to produce "humanized" antibody.

Alternatively, nucleic acid encoding Chi31.1-1 heavy and light chains (including human constant regions) may be inserted into various expression vectors to facilitate expression. Specific non-limiting examples of such PCR primers are:

a) for insertion of Chi31.1-1 light chain encoding sequences at a BamHl/XbaI insertion site:
  i) Chi31.1-LcBamHl (S):
  5'-ATA GGA TCC ATG AAG TCA CAG ACC CAG GTC TTC G-3' (SEQ ID NO:7)
  ii) Chi31.1-LcXBaI (A):
  5'-TTT CTA GAC TAA CAC TCT CCC CTG TTG AAG C-3' (SEQ ID NO:8)
b) for insertion of Chi31.1-1 heavy chain encoding sequences at a EcoRI/NotI insertion site:
  i) Chi31.1-HcEcoRI (S):
  5'-ATA GAA TTC ATG GCT TGG GTG TGG ACC TTG CT-3' (SEQ ID NO:9)

ii) Chi31.1-HcNotI (A): 5'-TTG CGG CCG CTC ATT TAC CCG GAG-3' (SEQ ID NO:10). Such primers may be used in polymerase chain reactions using, as template, DNA prepared from hybridoma cells deposited with the ATCC and assigned accession no. ATCC CRL-12316.

"Equivalents" of Mu-31.1 are defined herein as immunoglobulin molecules or fragments or derivatives thereof which compete with Mu-31.1 for binding to its target antigen, as evaluated using standard techniques. Such equivalents may include complete antibody molecules (i.e., having two heavy chains and two light chains), single chain antibody molecules (see, for example, Lee et al., 1999, Molec. Immunol. 36: 61-71, incorporated by reference herein), fragments such as F (ab) and F (ab) 2 fragments of Mu-31.1, Chi31.1-1, Chi31.1-2, or equivalent complete antibody molecules, and derivative molecules including, but not limited to, one or more of the foregoing immunoglobulin molecules or fragments conjugated to a bioactive agent, or modified to more closely resemble a human immunoglobulin molecule (see, for example; Ryu et al., 1996, Human Antibod. Hybridomas 7: 113122). Such equivalents, which include Mu-31.1, Chi31.1-1, Chi31.1-2, are collectively referred to as "31.1-Ab equivalents".

The use of co-specific antibodies and their equivalents (with equivalents having the same scope as that applied to the 31.1 antibody) is also envisioned according to the invention. A co-specific antibody to Mu-31.1 (referred to as "31.1 co-specific antibodies") may or alternatively may not compete with binding of Mu-31.1, but recognizes (i.e., binds to) the same target antigen, referred to herein as "31.1-Ag"). The co-specific antibodies to 31.1 and their equivalents are referred to herein as "31.1 co-specific antibody equivalents".

Any 31.1 antibody equivalent or 31.1 co-specific antibody equivalent to be used in humans preferably has a structure which itself does not provoke a deleterious immune reaction in humans. For example, said 31.1 antibody equivalent or 31.1 co-specific antibody equivalent may inherently lack such immunogenic structures or may be the product of a "humanization" process by standard techniques to minimize or eliminate structures which would be recognized as non-self by a subject (e.g. chimerization and/or site by site engineering). 31.1-Ag appears to be localized to the membrane of colon and pancreas cancers. Its presence has not been detected on normal human tissue obtained fresh and immediately frozen (TABLE A).

TABLE A

Cross-reactivity to normal fresh frozen human tissues.

| Tissue (number) | Staining paraffin | Staining frozen samples |
|---|---|---|
| Colon (3) | Negative (3) | Negative (2) Trace positive (1) |
| Small bowel (3) | Negative (3) | Negative (3) |
| Esophagus (3) | Negative (3) | Negative (3) |
| Oral Mucosa (2) | Negative (2) | Negative (2) |
| Jejunum (1) | Negative (1) | Negative (1) |
| Stomach (1) | Negative (1) | Negative (1) |
| Liver (3) | Negative(3) | Negative(3) |
| Pancreas (3) | Negative (3) | Negative (3) |
| Thymus (3) | Negative (3) | Negative(3) |
| Heart (2) | Negative (2) | Negative(2) |
| Prostate (2) | Negative (2) | Negative (2) |
| Breast (3) | Negative (3) | Negative (3) |
| Testis (1) | Negative (1) | Negative (1) |
| Ovary (2) | Negative (2) | Negative (2) |
| Salivary gland (3) | Negative (3) | Negative (3) |
| Spleen (2) | Negative (2) | Negative (2) |

TABLE A-continued

Cross-reactivity to normal fresh frozen human tissues.

| Tissue (number) | Staining paraffin | Staining frozen samples |
|---|---|---|
| Brain (3) | Negative (3) | Negative (3) |
| Lymph node (2) | Negative (2) | Negative (2) |
| Adrenal (1) | Negative (1) | Negative (1) |
| Vagina (1) | Negative (1) | Negative (1) |
| WBC (1) | Negative (1) | Negative (1) |

31.1-Ag is, however, found on the surface of colon and pancreas cancers obtained fresh at the moment of surgery and frozen (TABLE B).

TABLE B

Localization of 31.1 antigen on colon and pancreas cancers

| Cancer (number) | Staining paraffin | Staining frozen samples |
|---|---|---|
| Adenocarcinoma of colon | Positive (3) | Positive (3) |
| Adenocarcinoma of pancreas (3) | Positive (3) | Positive (3) |

It should be noted that this result differs from that presented in Table 2 of U.S. Pat. No. 5,688,657 (at column 24, lines 1-26), which indicates that antibody Mu-31.1 did not bind to either of two pancreas tumor samples tested. Table 1 of U.S. Pat. No. 5,688,657 (at column 23 lines 1-38) shows that Mu-31.1 reacted with two out of three pancreatic cancer-derived cell lines. Based on the information contained in U.S. Pat. No. 5,688,657, one may have concluded that 31.1 Ag only appeared after passage of the cells in culture, and was not present on fresh pancreatic cancer tissue. It is therefore unexpected, based on the disclosure of U.S. Pat. No. 5,688,657, that 31.1-Ag would be present on 3/3 pancreatic tumor samples, as set forth in TABLE B herein.

Mu-31.1 is secreted from a hybridoma cell line developed by fusion with the murine SP2 cell line cell-line. Mu-31.1, Chi31.1-1, and Chi31.1-2, 31.1-Ab equivalents, and 31.1 co-specific antibodies may be manufactured, for example and not by way of limitation, for clinical use by standard in vitro cell culture and downstream purification processes. For example, hybridoma cells may be grown in Geneticin (0.2 mg/ml) since the presence of the antibiotic has been observed to allow the hybridoma cells to grow better.

Preferably, compositions comprising the forgoing 31.1-Ab equivalents and 31.1 co-specific antibodies may be made without the addition of human additives. For example, the preparations may be filtered through a bacterial Millipore 0.2 micron filter to eliminate contaminants and verified as sterile for bacteria and fungi by streaking blood agar plates and culture media with positive controls for 14 days. The preparation may be determined to be free of *Mycoplasma* by, for example, PCR *Mycoplasma* assays and by *Mycoplasma* Agar plates (Life Technology cat #18042-010) and Myco Test Kit (Life Technology Cat #15672-017) using 3T6 control cells.

Media containing one or more of the foregoing 31.1-Ab equivalents or 31.1 co-specific antibodies may be filtered through a Pall endotoxin filter and the glassware heat sterilized to eliminate endotoxin. Desirably, but not by way of limitation, an appropriate endotoxin level may be 0.125 units/ml or less, as measured by the BioWhittaker Pyrogent 03,250 test kit.

In preferred, non-limiting embodiments of the invention, one of the foregoing preparations may be treated so as to inactivate virus. For example, retrovirus may be inactivated by acetic acid treatment at pH 3 for one hour during column chromatography and filtration through a Pall Ultipor Grade DV50 Virus Removal Filter of 10-40 nm.

In a specific, non-limiting embodiment of the invention, 50 mg of Ch31.1-1 is contained in a vial at a concentration of 2 mg/ml in phosphate buffered saline ("PBS").

5.2. Treatment Protocols

The present invention provides for the use of 31.1-Ab equivalents and/or 31.1 co-specific antibody equivalents, used singly or in combination, in the treatment of pancreas cancer in a subject in need of such treatment. The method involves administering, to the subject, a therapeutically effective dose of one or more 31.1-Ab equivalent and/or 31.1 co-specific antibody equivalent. A therapeutically effective dose is defined, herein, as a dose which achieves one or more of the following in the subject: produces detectable pancreatic carcinoma cell lysis in the subject; causes a decrease in the growth, or invasiveness, or size of a pancreas tumor; causes an improvement in clinical symptoms; and/or causes an increase in survival time. Preferably, but not by way of limitation, a single dose of 31.1-Ab equivalent and/or 31.1 co-specific antibody equivalent may range from about 25 mg to about 1000 mg, and preferably from about 100 mg to 250 mg. The magnitude of the dose may be adjusted on a patient-by-patient basis to avoid undesirable side effects and/or toxicity. It is preferred that the 31.1-Ab equivalent and/or 31.1 co-specific antibody equivalent is administered as a series (plurality) of single doses, administered at intervals of between about 1 and 4 weeks, preferably every two weeks, until side effects rise to an undesirable level or disease progresses to an undesirable level. The 31.1-Ab equivalent and/or 31.1 co-specific antibody equivalent may be administered via any standard route; preferably, to test whether a patient tolerates the formulation (i. e., the patient does not manifest an undesirable allergic and/or other toxic reaction), it may first be administered subcutaneously, and once adequate tolerance is shown, it may be administered intravenously.

In one specific, non-limiting example, a protocol according to the invention may be as follows.

Using aseptic procedures, a "humanized" 31.1-Ab equivalent and/or 31.1 co-specific antibody equivalent, produced using standard biotechnology techniques, may be filtered through a 0.22 micron low protein filter into a glass infusion bottle or non-DEEP-containing infusion bag containing 0.9% sodium chloride to a final concentration of 0.4 mg/ml. The infusate may be mixed gently. If the infusion is observed to be cloudy, it should not be administered.

To determine whether a patient tolerates treatment with the "humanized" 31.1-Ab equivalent or 31.1 co-specific antibody equivalent, the patient may be pre-medicated with diphenhydramine 25 mg i.v. and paracetamol 650 mg p.o., and then 30 micrograms of 31.1-Ab equivalent or 31.1 co-specific antibody equivalent may be injected subcutaneously. If no allergic toxicity or a grade 1 allergic toxicity occurs, intravenous treatment will proceed. If a grade 1 allergic toxicity occurs, resolution of the toxicity will be necessary prior to proceeding with the intravenous injection.

If the patient tolerates the subcutaneous test dose described in the preceding paragraph, the patient may be treated with a first infusion of 25 mg of the 31.1-Ab equivalent or 31.1 co-specific antibody equivalent over 2 hours. Premedication in the form of diphenhydramine 25 mg i.v. and paracetamol 650 mg p.o. may be given. The patient may then be observed for any potential side effects for 6 hours after the injection. The patient may be monitored with vital signs prior to the injection, and every 15 minutes during the first hour of treatment, every 30 minutes for two hours thereafter, and every hour thereafter until 6 hours after completion of the infusion.

If the first infusion has been found to be tolerated, after 2 weeks, the patient may then receive an infusion of 50 mg of the 31.1-Ab equivalent or 31.1 co-specific antibody equivalent, in a volume of 100 cc PBS or other suitable diluent, over 4 hours using the same clinical protocol as set forth in the preceding paragraph. If this second infusion has also been found to be tolerated, the patient may then receive infusions of 100 mg of the 31.1-Ab equivalent or 31.1 co-specific antibody equivalent in 100 cc diluent over 4 hours every two weeks, using the above-described protocol. The patient may then continue such treatment until intolerance develops or progression of disease occurs, and preferably for a maximum of 4 months. If any grade 3 or higher toxicity occurs due to the treatment, the patient may discontinue treatment permanently. If it is deemed that the toxicity is not treatment related, the patient may be able to resume treatment upon recovery of the toxicity. If any grade 2 toxicity occurs during or after treatment, the infusion may desirably be stopped. If recovery to grade 0 occurs, the infusion may then be restarted. If recovery has not occurred by the time of the next planned treatment, treatment may be delayed until recovery to grade 0 has occurred. If recovery to grade 0 does not occurred within 4 weeks, treatment may be discontinued permanently. If any allergic reaction of grade 2 or higher occurs, the treatment may be stopped and preferably no further infusion may be given.

In specific non-limiting embodiments of the invention, the following may serve as criteria for patients suitable for treatment:

a) the patient may suffer from a histologically confirmed recurrent or metastatic adenocarcinoma of the pancreas, where the tumor reacts with the 31.1-Ab equivalent or 31.1 co-specific antibody intended to be used;

b) treatment of the patient by a standard regimen for metastatic pancreas cancer may have failed;

c) disease in the patient may be measurable by one or more of the following:
  i) physical examination;
  ii) computerized tomography or other radiological study;
  iii) CEA levels; and/or
  iv) Ca 19-9 levels;

d) the patient may be 18 years of age or older;

e) the patient may exhibit a WHO performance status of 0, 1, or 2;

f) the prognosis of the patient may indicate a life expectancy of at least 12 weeks;

g) hematological testing of the patient may indicate the following values:
  i) WBC>3,000;
  ii) HGB>10; and
  iii) platelets>100,000;

h) clinical chemistry values may be as follows:
Creatinine, bilirubin, aspartate transaminase, alanine transaminase, alkaline phosphatase, and bilirubin are all less than or equal to 2 times upper limit of normal; and/or i) the patient has adequate peripheral venous access for repeated blood sampling.

In specific non-limiting embodiments of the invention, the following may serve as criteria for excluding patients who may be unsuitable for treatment:

a) less than 4 weeks may have elapsed since prior chemotherapy (or 6 weeks for nitrosoureas or mitomycin-C), since treatment with biological response modifiers or since radiation therapy;

b) the patient is currently receiving steroid therapy c) the patient is pregnant (men and women on the study, if fertile, are counseled to practice effective contraception);

d) the patient is a lactating female;

e) the patient suffers from a debilitating non-malignant co-morbid condition, such as active infection or an acute intercurrent complication of malignancy;

f) there is central nervous system involvement;

g) the patient has previously received a bone marrow or other organ transplant;

h) the patient has a history of another malignancy, except for adequately treated non-melanoma cancer of the skin or in situ cancer of the cervix;

i) the patient has previously been exposed to murine monoclonal or polyclonal antibodies; and/or j) the patient is known to be HIV positive.

During the course of the study, non-limiting examples of adverse reactions include shortness of breath, hypotension, cyanosis, rash, bronchospasm, chills, rigors, back pain, fever, cyanosis, nausea, vomiting, palpitations or any other adverse reaction.

In non-limiting embodiments of the invention, the following laboratory tests may desirably be performed to evaluate patients being treated by the protocol. With regard to hematology tests, a complete blood count, differential, and platelet count may be obtained prior to each infusion and weekly during treatment until four weeks after the last injection. With regard to clinical chemistry tests, a complete chemistry panel measuring glucose, sodium, potassium, bicarbonate, chloride, blood urea nitrogen, creatinine, uric acid, calcium, inorganic phosphate, total protein, albumin, lactate dehydrogenase, aspartate transaminase, alanine transaminase and alkaline phosphatase may be obtained weekly during treatment and until four weeks after the last injection. With regard to special laboratory tests, serum samples obtained from 10 cc of blood may be collected before and within two minutes of each injection, at times 15 min, 30 min, 60 min, 2, 4, 24 and 72 hours after completion of the first injection and every two weeks thereafter prior to each injection and until four weeks after the last treatment and processed for the detection of administered 31-1-Ab equivalent and/or 31.1 co-specific antibody equivalent. These serum samples may then be used to determine ADCC, antibody concentration, and the presence of human antibodies directed toward the administered antibody equivalent. Urinalysis may be performed at enrollment and before each of the injection as well as four weeks after the last injection, with microscopic examination performed on any abnormal specimens.

In various embodiments of the invention, the following safety assessments may desirably be made. For each of infusion, vital signs including the temperature, pulse and blood pressure of the patient may be obtained prior to and after each infusion. The pulse and blood pressure may be recorded every fifteen minutes during the first hour of infusion and then every half hour for two hours, followed by hourly until 6 hours after the completion of the infusion. Patients may be observed and vital signs monitored until six hours after the completion of the infusion or until return to baseline of the vital signs.

An initial evaluation and subsequent evaluations of the patient's response to treatment may be performed as follows. Tumor measurement may be performed by physical examination and or standard or special radiological studies such as chest X-ray, computerized tomography, magnetic resonance imaging, or ultrasound. If more than one measurable lesion exists, representative lesions should be measured. The longest perpendicular measurements of the representative lesions may be recorded prior to treatment and every eight weeks. Levels of Ca 19.9 may be monitored regularly, for example monthly.

Preferably written informed consent is obtained for each patient to be treated. Each patient should be given a verbal description of the treatment, its potential risks and benefits as well as alternative treatments available, prior to signing the written consent.

During the course of treatment, blood products, antibiotics, antiemetic, analgesics or other medications for stable coexisting medical conditions may be administered as appropriate.

The treatment may be discontinued in a patient if there is evidence of progressive disease, if a serious or unexpected adverse reaction occurs, or for other medically appropriate reasons.

In addition to the therapeutic uses described herein, the 31.1 antibodies and functional equivalents thereof may be used to diagnose pancreatic carcinoma in a subject. The diagnostic methods of the invention are based on the discovery that the 31.1 antibody selectively binds to an antigen expressed in pancreatic carcinoma cells but not normal cells.

In accordance with the invention, measurement of levels of monoclonal antibody 31.1 reactivity in samples derived from a subject can be used for the diagnosis of diseases such as pancreatic carcinoma. The detection of monoclonal 31.1 antibody reactivity in a sample from a subject can be accomplished by any of a number of methods. Preferred diagnostic methods can involve, for example, immunoassays wherein 31.1 reactive antigen is detected by their interaction with an 31.1 monoclonal antibody. Immunoassays useful in the practice of the invention include but are not limited to assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

A biological sample, such as pancreatic tissue or other biological tissue, is obtained from a subject suspected of having a particular cancer or risk for cancer. Aliquots of whole tissues, or cells, are solubilized using any one of a variety of solubilization cocktails known to those skilled in the art. For example, tissue can be solubilized by addition of lysis buffer comprising (per liter) 8 M urea, 20 ml of Nonidet P-40 surfactant, 20 ml of ampholytes (pH 3.5-10), 20 ml of 2 mecaptoethanol, and 0.2 mM of phenylmethylsulfonyl fluoride (PMSF) in distilled deionized water.

Immunoassays for detecting expression of the 31.1 reactive antigen typically comprise contacting the biological sample, such as a tissue sample derived from a subject, with the 31.1 monoclonal antibody under conditions such that an immunospecific antigen-antibody binding reaction can occur, and detecting or measuring the amount of any immunospecific binding by the antibody. In a specific aspect, such binding of antibody, for example, can be used to detect the presence and increased production of 31.1 reactive antigen wherein the detection of the antigen is an indication of a diseased condition.

6. EXAMPLE: PREPARATION OF PRC/CMV VECTOR

The pRc/CMV vector was prepared using a series of plasmids, as depicted in FIG. 1A-F. The heavy and light chains of Chi31.1-1 were cloned into the pCR vector (FIG. 1A) by TOPO (Topoisomerase I) cloning. Sequences used for inserting the light and heavy chain sequences into the pCR vector by PCR are as follows:

```
a) for insertion of the Chi31.1-1 light chain
encoding region at a BamH1/XbaI insertion site:
i) Chi31.1-LcBamH1 (S):
                                        (SEQ ID NO: 7)
5'-ATA GGA TCC ATG AAG TCA CAG ACC CAG GTC TTCG-3' ii) Chi31.1-LcXBaI (A):
                                        (SEQ ID NO: 8)
5'-TTT CTA GAC TAA CAC TCT CCC CTG TTG AAG C-3' b) for insertion of the Chi31.1-1 heavy chain
encoding region at a EcoRI/NotI insertion site:
i) Chi31.1-HcEcoRI (S):
                                        (SEQ ID NO: 9)
5'-ATA GAA TTC ATG GCT TGG GTG TGG ACC TTG CT-3' ii) Chi31.1-HcNotI (A):
                                        (SEQ ID NO: 10)
5'-TTG CGG CCG CTC ATT TAC CCG GAG-3'
```

These were then cloned from the pCR vector into the pDCM-dhfr vector, such that the light chain encoding region was inserted at the BamHl/Xbal site (under the control of the cytomegalovirus ("CMV") promoter, and the heavy chain encoding region was inserted into the EcoRI/Notl site, under the control of a second CMV promoter element (FIG. 1F).

The pDCM-dhfr vector was prepared using the series of steps set forth in FIGS. 1B-E. A series of vector constructions using some related components are described in Ryu et al., 1996, Hum. Antibod. Hybridomas 7: 113-122 (based on the pRc/CMV vector (Invitrogen); see, for example, page 115 and FIG. 4 of Ryu et al.); Jin et al., 1995, Virus Res. 38: 269; and Lee et al., 1999, Molec. Immunol. 36: 61-71 (see, for example, FIG. 2 of that publication).

Basically, the pcDNA3 vector (Invitrogen) (FIG. 1B) was used as the basis for the pDCM vector (FIG. 1C), in that digestion with pairs of restriction enzymes followed by re-ligation was used, in parallel preparations, to destroy certain cleavage sites and maintain others in vector downstream of the CMV promoter sequences. Specifically, as shown in FIG. 1C, digestion of pcDNA3 with first HindIII and BamHI, followed by religation and then digestion with Hot and Apia, followed by religation, resulted in the preservation of Bestir, EcoRI, EcoRV, BstXI, and NotI sites downstream of the promoter; subsequent cleavage with BsmI linearized the molecule between the ampicillin and neomycin resistance genes (component 1). In parallel, digestion of pcDNA3 with Bstxl and NotI, followed by removal of the small fragment and re-ligation, removed the BstXI, EcoRI, EcoRV, BstXI, and NotI sites and left the HindIII, KpnI, BamHI, XhoI, Xbal and ApaI sites intact; cleavage with PvuII and NruI gave rise to a fragment containing the CMV promoter, the preserved sites, and BGHpA (component 2). Component 2 was inserted between the ends of component 1, resulting in pDCM, having two different insertion sites for genes downstream of two respective CMV promoter elements. As shown in FIG. 1E, a dihydrofolate reductase gene ("dhfr") from KC-dhfr may then be inserted into pDCM (see Lee et al., 1999, Molec. Immunol. 36:61-71) to produce pDCM-dhfr. Alternatively, as shown in FIG. 1D, the dhfr gene from KC-dhfr may be incorporated into pcDNA3, to produce pCdhfr, which may then be engineered by methods analogous to those shown in FIG. 1C to produce the two CMV promoter/insertion site cassette.

The Chi31.1-1 heavy and light chain encoding sequences were then cloned from the pCR vector into pDCM-dhfr, to form pRc/CMV, which may be transfected into CHO dhfr-cells, after which expressed chimeric immunoglobulin molecules may be collected according to standard techniques.

7. EXAMPLE: HUMAN IMMUNE RESPONSE TO CHI31.1-1

To determine whether the 31.1 chimeric antibodies are capable of inducing an immune response, plasma was collected from a human subject who had been administered Chi31.1-1 chimeric monoclonal antibody. The presence of an immune reaction in the patient toward the chimeric antibody was tested using the following assay.

96 well microtiter plates were coated with Chi31.1-1 antibody, using a solution which was 10 micrograms per milliliter, with 100 microliters per well. A preparation of Chi31.1-1 was biotinylated. Then, either control plasma or patient plasma (50 microliters) was introduced into wells, and 50 microliters of the biotinylated Chi31.1-1 was added. The plates were then incubated for ninety minutes at 37 degrees centigrade and then the wells were washed and streptavidin-horseradish peroxidase conjugate was added. The wells were then washed three times. Then TMB substrate (3,3',5,5' tetramethyl benzidine) was added, and the plates were incubated for 20 minutes. Stop solution was added, and the amount of reacted substrate was determined.

The results are presented in TABLE C, and are expressed in nanograms of Chi31.1-1 bound per milliliter of plasma. Results greater than 2-fold above the pre-treatment baseline are considered to be positive. Non-specific baseline binding values from 3 healthy normal samples were found to be 4 plus or minus 2 nanograms per milliliter. The standard was determined by using goat anti-human IgGI coated wells with various concentrations of biotinylated Chi31.1-1 monoclonal antibody.

TABLE C

Human Immune Response to Chi31.1-1 Monoclonal Antibody (HAMA)

| Time | ng/ml bound |
|---|---|
| 0 hour (pretreatment) | 2 |
| 1 hour | 3 |
| 2 hours | 2 |
| 3 hours | 3 |
| 4 hours | 3 |
| 5 hours | 2 |
| 6 hours | 3 |
| Next day | 4 |
| 1 week | 3 |
| 2 weeks | 5 |

8. EXAMPLE: ADCC ACTIVITY OF CHO CHI31.1 ANTIBODY

The following section describes experiments demonstrating that the CHO Chi31.1 monoclonal antibody has biological activity associated with destruction of tumors. Specifically, the antibody was shown to have antibody-dependent cellular cytotoxicity (ADCC).

A four hour $^{111}$In release assay was used to measure ADCC activity. Target cells were the colon tumor cell line SW1643 and pancreatic cancer cell line PANC-1. UPC-10 was used as a control antibody. Target cells were labeled with 50 µCi of $^{111}$In-oxyquinoline for 15 minutes at room temperature. Target cells (1×10$^4$) in 50 µl were added to 96-well plate. Ratios of effector to target cells of 100:1, 50:1 and 25:1 were assayed in the presence of CHO31.1 (1 mg/well). The plates were incubated for four hours at 37° C. in a humidified atmosphere containing 5% $CO_2$. Supernatant was harvested for gamma counting with the use of Skatron Harvester frames. Experiments were carried out in triplicate.

Specific lysis was calculated with the use of the following formula:

$$\% \text{ lysis} = 100 \times \frac{\text{observed release}(cpm) - \text{spontaneous release}(cpm)}{\text{total release }(cpm) - \text{spontaneous release}(cpm).}$$

As presented in FIGS. 6A and 6B, the CHO 31.1 antibody, but not the control UPC-10 antibody, was capable of mediating antibody-dependent cellular cytotoxicity against the target cells.

Various publications are cited herein, the contents of which are hereby incorporated by reference in their entireties herein.

---

What is claimed is:

1. A method of killing cells that express a pancreatic carcinoma associated antigen, comprising delivering to said cells an effective amount of a 31.1 monoclonal antibody, wherein said antibody is specific for pancreatic cancer cells.

2. The method of claim 1, wherein said cells are killed in a subject or are cultured cells.

3. The method of claim 1, wherein:
   (a) the light chain of said antibody is encoded by the nucleotide sequence SEQ ID NO: 1, SEQ ID NO: 3, or a humanized variant of SEQ ID NO: 1 or SEQ ID NO: 3; and
   (b) the heavy chain of said antibody is encoded by the nucleotide sequence of SEQ ID NO: 4, SEQ ID NO: 6, or a humanized variant of SEQ ID NO: 4 or SEQ ID NO: 6;
   or wherein said chimerized antibody is expressed by a cell line deposited under ATCC Accession Number CRL-12316.

4. The method of claim 1, wherein said antibody is a recombinant, chimerized, co-specific, or humanized antibody.

5. The method of claim 1, wherein said antibody is selected from the group consisting of a single chain antibody, a F(ab) fragment, and a F(ab)$_2$ fragment.

6. The method of claim 1, wherein the light chain of said antibody is encoded by the nucleotide sequence of SEQ ID NO: 1, SEQ ID NO: 3, or a humanized variant of SEQ ID NO: 1 or SEQ ID NO: 3, and/or wherein the heavy chain of said antibody is encoded by the nucleotide sequence of SEQ ID NO: 4, SEQ ID NO: 6, or a humanized variant of SEQ ID NO: 4 or SEQ ID NO: 6.

7. The method of claim 1, wherein said antibody or fragment is conjugated to a bioactive agent.

8. The method of claim 1, wherein said method further comprises physical examination or a radiological study to detect the presence of pancreatic cancer in said subject.

9. The method of claim 8, wherein said radiological study comprises a chest X-ray, computerized tomography, magnetic resonance imaging, or ultrasound.

10. The method of claim 8, wherein said subject has recurrent or metastatic adenocarcinoma of the pancreas.

11. The method of claim 8, wherein said subject has cancer or is at risk for cancer.

12. The method of claim 3, wherein said antibody is a chimerized or humanized antibody.

13. The method of claim 3, wherein said antibody is selected from the group consisting of a single chain antibody, a F(ab) fragment, and a F(ab)$_2$ fragment.

14. The method of claim 3, wherein the light chain of said antibody is encoded by the nucleotide sequence of SEQ ID NO: 1, SEQ ID NO: 3, or a humanized variant of SEQ ID NO: 1 or SEQ ID NO: 3, and/or wherein the heavy chain of said antibody is encoded by the nucleotide sequence of SEQ ID NO: 4, SEQ ID NO: 6, or a humanized variant of SEQ ID NO: 4 or SEQ ID NO: 6.

15. The method of claim 3, wherein said antibody or fragment is conjugated to a bioactive agent.

16. The method of claim 3, wherein said method further comprises physical examination or a radiological study to detect the presence of pancreatic cancer in said subject.

17. The method of claim 16, wherein said radiological study comprises a chest X-ray, computerized tomography, magnetic resonance imaging, or ultrasound.

18. The method of claim 3, wherein said antibody is administered to a subject having recurrent or metastatic adenocarcinoma of the pancreas.

19. The method of claim 3, wherein said antibody is administered to a subject having cancer or at risk for cancer.

* * * * *

SEQUENCE LISTING

```
<160> NUMBER OF SEQ ID NOS: 10

<210> SEQ ID NO 1
<211> LENGTH: 384
<212> TYPE: DNA
<213> ORGANISM: Homo sapien

<400> SEQUENCE: 1
atgaagtcac agacccaggt cttcgtattt ctactgctct gtgtgtctgg tgctcatggg     60
agtattgtga tgacccagac tcccaaattc ctgcttgtat cagcaggaga cagggttacc    120
ataacctgca aggccagtca gagtgtgagt aatgatgtag cttggtacca acagaaacca    180
gggcagtctc ctaaactgct gatatactat gcatccaatc gctacactgg agtccctgat    240
cgcttcactg gcagtggata tgggacggat ttcactttca ccatcagcac tgtgcaggct    300
gaagacctgg cagtttattt ctgtcagcag gattatagct ctccgctcac gttcggtgct    360
gggaccaagc tggagctgaa acgt                                           384

<210> SEQ ID NO 2
<211> LENGTH: 384
<212> TYPE: DNA
<213> ORGANISM: Homo sapien
<220> FEATURE:
<221> NAME/KEY: misc_feature
<222> LOCATION: (0)..(0)
<223> OTHER INFORMATION: Antisense strand

<400> SEQUENCE: 2
acgtttcagc tccagcttgg tcccagcacc gaacgtgagc ggagagctat aatcctgctg     60
acagaaataa actgccaggt cttcagcctg cacagtgctg atggtgaaag tgaaatccgt    120
cccatatcca ctgccagtga agcgatcagg gactccagtg tagcgattgg atgcatagta    180
tatcagcagt ttaggagact gccctggttt ctgttggtac caagctacat cattactcac    240
actctgactg gccttgcagg ttatggtaac cctgtctcct gctgatacaa gcaggaattt    300
gggagtctgg gtcatcacaa tactcccatg agcaccagac acacagagca gtagaaatac    360
gaagacctgg gtctgtgact tcat                                           384

<210> SEQ ID NO 3
<211> LENGTH: 128
<212> TYPE: PRT
<213> ORGANISM: Homo sapien

<400> SEQUENCE: 3
```

```
Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
                100                 105                 110

Ser Ser Pro Leu Thr Phe Gly Ala Gly Thr Lys Leu Glu Leu Lys Arg
            115                 120                 125
```

<210> SEQ ID NO 4
<211> LENGTH: 411
<212> TYPE: DNA
<213> ORGANISM: Homo sapien

<400> SEQUENCE: 4

```
atggcttggg tgtggacctt gctattcctg atggcagctg cccaaagtgc ccaagcacag      60
atccagttgg tgcagtctgg acctgagctg aagaagcctg agagacagt caagatctcc    120 tgcaaggctt ctgggtatac cttcacaaac tatggaatga actgggtgaa gcaggctcca    180
ggaaagggtt taaagtggat gggctggata aacacctaca ctggagagcc aacatatgct    240
gatgacttca aggacggtt tgccttctct ttggaaacct ctgccagcac tgcctatttg     300
cagatcaaca acctcaaaaa tgaggacacg gctacatatt tctgtgcaag agcctactat    360
ggtaaatact ttgactactg gggccaaggc accactctca cagtctcctc a             411
```

<210> SEQ ID NO 5
<211> LENGTH: 411
<212> TYPE: DNA
<213> ORGANISM: Homo sapien
<220> FEATURE:
<221> NAME/KEY: misc_feature
<222> LOCATION: (0)..(0)
<223> OTHER INFORMATION: antisense strand

<400> SEQUENCE: 5

```
tgaggagact gtgagagtgg tgccttggcc ccagtagtca agtatttac catagtaggc      60 tcttgcacag aaatatgtag ccgtgtcctc attttgagg ttgttgatct gcaaataggc     120
agtgctggca gaggtttcca agagaaggc aaaccgtccc ttgaagtcat cagcatatgt     180
tggctctcca gtgtaggtgt ttatccagcc catccacttt aaacccttc ctggagcctg     240 cttcacccag ttcattccat agtttgtgaa ggtataccca gaagccttgc aggagatctt    300
gactgtctct ccaggcttct tcagctcagg tccagactgc accaactgga tctgtgcttg    360
ggcactttgg gcagctgcca tcaggaatag caaggtccac acccaagcca t             411
```

<210> SEQ ID NO 6
<211> LENGTH: 137
<212> TYPE: PRT
<213> ORGANISM: Homo sapien

<400> SEQUENCE: 6

```
Met Ala Trp Val Trp Thr Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
            35                  40                  45

Thr Asn Tyr Gly Met Asn Trp Val Lys Gln Ala Pro Gly Lys Gly Leu
50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Ala Tyr Tyr Gly Lys Tyr Phe Asp Tyr Trp Gly
            115                 120                 125

Gln Gly Thr Thr Leu Thr Val Ser Ser
    130                 135
```

<210> SEQ ID NO 7
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 7
ataggatcca tgaagtcaca gacccaggtc ttcg         34

<210> SEQ ID NO 8
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 8
tttctagact aacactctcc cctgttgaag c            31

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 9
atagaattca tggcttgggt gtggaccttg ct           32

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 10
ttgcggccgc tcatttaccc ggag                    24